US012653537B2

(12) United States Patent　　(10) Patent No.:　US 12,653,537 B2
Thornton　　(45) Date of Patent:　*Jun. 16, 2026

(54) DEVICE AND METHOD FOR VARIABLE BLOOD FLOW OCCLUSION

(71) Applicant: Cardio-Renal Solutions, Inc., San Francisco, CA (US)

(72) Inventor: Troy Thornton, San Francisco, CA (US)

(73) Assignee: Cardio -Renal Solutions, Inc., San Francisco, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 17/692,007

(22) Filed: Mar. 10, 2022

(65) Prior Publication Data

US 2022/0287831 A1　　Sep. 15, 2022

Related U.S. Application Data

(60) Provisional application No. 63/160,637, filed on Mar. 12, 2021.

(51) Int. Cl.
A61B 17/12　　　(2006.01)
A61F 2/06　　　(2013.01)
(Continued)

(52) U.S. Cl.
CPC .. A61B 17/12036 (2013.01); A61B 17/12022 (2013.01); A61B 17/12109 (2013.01);
(Continued)

(58) Field of Classification Search
CPC .. A61F 2002/0068; A61F 2/07; A61F 2/2418; A61F 2/01; A61F 2/0103;
(Continued)

(56)　　　　　References Cited

U.S. PATENT DOCUMENTS 4,546,759 A　　10/1985　Solar
6,193,748 B1　　2/2001　Thompson et al.
(Continued)

FOREIGN PATENT DOCUMENTS

CA　　　　2422915 C　*　5/2007　............... A61F 2/06
WO　WO2020/023514 A1　　1/2020
(Continued)

OTHER PUBLICATIONS

Thornton; U.S. Appl. No. 17/852,010 entitled "Device and method for variable blood flow occlusion," filed Jun. 28, 2022.

*Primary Examiner* — Sarah W Aleman
*Assistant Examiner* — Rachel S Highland
(74) *Attorney, Agent, or Firm* — Shay Glenn LLP

(57)　　　　　ABSTRACT

A blood flow control device having a catheter adapted to be advanced into a blood vessel to a blood flow control site within the blood vessel; an expandable anchor supported by the catheter, the expandable anchor being adapted to expand to engage a wall of the blood vessel, the expandable anchor having a blood impermeable wall defining an adjustable blood flow path extending through the expandable anchor from a proximal opening to a distal opening, the catheter being disposed outside of the adjustable blood flow path; a flow control element supported by the catheter, the flow control element being adapted to change a dimension of the adjustable blood flow path to change a rate of blood flow through the blood flow path; and a blood flow control actuator disposed at a proximal section of the catheter and adapted to actuate the flow control element.

18 Claims, 20 Drawing Sheets

(51) Int. Cl.
    *A61F 2/07*          (2013.01)
    *A61F 2/24*          (2006.01)
    *A61F 2/90*          (2013.01)

(52) U.S. Cl.
    CPC .................. *A61F 2/07* (2013.01); *A61F 2/90*
        (2013.01); *A61F 2002/068* (2013.01); *A61F*
        *2/2418* (2013.01); *A61F 2220/0016* (2013.01);
        *A61F 2220/0075* (2013.01); *A61F 2250/001*
        (2013.01); *A61F 2250/0013* (2013.01); *A61F*
        *2250/0039* (2013.01)

(58) Field of Classification Search
    CPC ........ A61F 2/0105; A61F 2/011; A61F 2/013;
        A61F 2/90; A61F 2002/068; A61F
        2220/0016; A61F 2220/0075; A61F
        2250/001; A61F 2250/0013; A61F
        2250/0039; A61F 2002/9511; A61F
        2002/9665; A61F 2230/001; A61F 2/966;
        A61B 17/1204; A61B 17/12027; A61B
        17/12013; A61B 17/12045; A61B
        17/12109; A61B 17/12122; A61B
        17/12036; A61B 17/12022
    See application file for complete search history.

(56)             References Cited

U.S. PATENT DOCUMENTS

| | | | |
|---|---|---|---|
| 8,968,239 | B2 | 3/2015 | Herrera |
| 9,393,384 | B1 | 7/2016 | Kapur et al. |
| 9,414,842 | B2 | 8/2016 | Glimsdale et al. |
| 9,675,474 | B2 | 6/2017 | McGuckin et al. |
| 10,363,044 | B2 | 7/2019 | Tal et al. |
| 10,758,715 | B2 | 9/2020 | Kapur et al. |
| 10,842,974 | B2 | 11/2020 | Kapur et al. |
| 10,898,698 | B1 | 1/2021 | Eigler et al. |
| 11,638,585 | B2 * | 5/2023 | Thornton ......... A61B 17/12109 623/1.15 |
| 2003/0023200 | A1 | 1/2003 | Barbut et al. |
| 2003/0032976 | A1 * | 2/2003 | Boucek ............ A61B 17/12172 623/1.18 |
| 2004/0116996 | A1 * | 6/2004 | Freitag ...................... A61F 2/88 623/1.11 |
| 2004/0249335 | A1 | 12/2004 | Faul et al. |
| 2005/0055082 | A1 | 3/2005 | Ben Muvhar et al. |
| 2005/0137699 | A1 * | 6/2005 | Salahieh ............... A61F 2/2418 623/2.11 |
| 2006/0064059 | A1 | 3/2006 | Gelfand et al. |
| 2007/0299465 | A1 * | 12/2007 | Messal ................... A61F 2/011 606/200 |
| 2009/0131785 | A1 | 5/2009 | Lee et al. |
| 2009/0187240 | A1 * | 7/2009 | Clerc ...................... A61F 2/848 623/1.22 |
| 2009/0210047 | A1 * | 8/2009 | Amplatz ................... A61F 2/07 623/1.13 |
| 2013/0090714 | A1 * | 4/2013 | McHugo ................... A61F 2/95 623/1.11 |
| 2013/0261531 | A1 | 10/2013 | Gallagher et al. |
| 2014/0172069 | A1 | 6/2014 | Roeder et al. |
| 2014/0277573 | A1 * | 9/2014 | Gill ...................... A61F 2/2476 623/23.68 |
| 2017/0056175 | A1 * | 3/2017 | Chin ..................... A61F 2/2427 |
| 2017/0367855 | A1 * | 12/2017 | Jenni ......................... A61F 2/90 |
| 2018/0085128 | A1 | 3/2018 | Bellomo et al. |
| 2018/0116839 | A1 | 5/2018 | McHugo et al. |
| 2018/0116848 | A1 | 5/2018 | McHugo et al. |
| 2018/0280667 | A1 * | 10/2018 | Keren .................... A61B 17/11 |
| 2019/0231568 | A1 | 8/2019 | Garcia |
| 2020/0178978 | A1 | 6/2020 | Ben-Muvhar et al. |
| 2020/0237538 | A1 | 7/2020 | Syed |
| 2020/0297516 | A1 | 9/2020 | Bellomo et al. |
| 2021/0177426 | A1 | 6/2021 | Tal |
| 2021/0186517 | A1 | 6/2021 | Tal et al. |
| 2022/0061852 | A1 | 3/2022 | Shohat et al. |

FOREIGN PATENT DOCUMENTS

| | | |
|---|---|---|
| WO | WO2020/121309 A1 | 6/2020 |
| WO | WO2020/214416 A1 | 10/2020 |
| WO | WO2021/226014 A2 | 11/2021 |

* cited by examiner

DEVICE AND METHOD FOR VARIABLE BLOOD FLOW OCCLUSION

CROSS REFERENCE TO RELATED APPLICATIONS

This application claims the benefit of U.S. Application No. 63/160,637, filed Mar. 12, 2021, the disclosure of which is incorporated herein by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

In patients with heart failure, reduced cardiac output can lead to reduced renal perfusion, which in turn can cause decreased urine output, activation of the sympathetic nervous system, and other neurohormonal changes. These compensatory mechanisms may occur in an attempt by the body to increase the blood volume to help maintain cardiac output. However, the increased blood volume can be detrimental, particularly because it increases venous pressure. The increased venous pressure can cause, for example, pulmonary and systemic edema or venous congestion. Higher venous pressure can also make it more difficult for the kidneys to function to remove fluid.

Increased venous pressure, or increased preload on the right heart, is thus detrimental to the recovery of heart failure patients. Accordingly, decreasing preload on the right heart is desired, as decreased preload lowers the cardiac filling pressure and increases cardiac output. Decreased venous pressure can also decrease renal vein pressure, increasing the pressure differential across the kidneys, which may enhance diuresis of the patient.

Many patients in heart failure are treated with diuretic drugs to reduce blood volume and venous pressure in order to reduce edema, but diuretic drugs are frequently ineffective, especially in patients with renal dysfunction or diuretic resistance. Device-based therapies have also been proposed, including devices that expand within a blood vessel, such as the inferior vena cava or the superior vena cava, to partially occlude the blood vessel for an extended time or to completely occlude the blood vessel for a short time.

SUMMARY OF THE DISCLOSURE

Described herein is a catheter-based blood flow control device that can be placed either in the superior vena cava (SVC) to decrease blood flow returning from the head and upper extremities or in the inferior vena cava (IVC) in an infrarenal location in order to decrease blood flow returning from the lower extremities. The device can restrict blood flowing in the antegrade direction, resulting in a higher pressure on the inflow (proximal) side and a lower pressure on the outflow (distal) side.

One aspect of the invention provides a blood flow control device having a catheter adapted to be advanced into a blood vessel to a blood flow control site within the blood vessel; an expandable anchor supported by the catheter, the expandable anchor being adapted to expand to engage a wall of the blood vessel, the expandable anchor including a blood impermeable wall defining an adjustable blood flow path extending through the expandable anchor from a proximal opening to a distal opening, the catheter being disposed outside of the adjustable blood flow path; a flow control element supported by the catheter, the flow control element being adapted to change a dimension of the adjustable blood flow path to change a rate of blood flow through the blood flow path; and a blood flow control actuator disposed at a proximal section of the catheter and adapted to actuate the flow control element. In some embodiments, the flow control element is adapted to change a shape of the adjustable blood flow path.

In some embodiments, the flow control element is adapted to change a shape of the expandable anchor. In some such embodiments, the flow control element includes a cinching line extending proximally from the expandable anchor and adapted to reduce a diameter of at least a portion of the expandable anchor. The cinching line may optionally extend from the actuator through a lumen of the catheter to an exit port on an exterior side of the catheter. In various embodiments, the flow control element is adapted to change a shape of a central portion of the expandable anchor, a shape of a distal portion of the expandable anchor, and/or a shape of a proximal portion of the expandable anchor.

In some or all of these embodiments, the flow control element is supported by the catheter outside of the adjustable blood flow path.

In some embodiments, the expandable anchor is disposed on an exterior side of the catheter at a distal section of the catheter such that the catheter is outside of the anchor. In some such embodiments, the blood flow control device also includes a sliding connector between the expandable anchor and the catheter adapted to permit at least one end of the expandable anchor to move longitudinally with respect to the catheter when the expandable anchor expands or collapses. A sliding connector may be disposed at a proximal end of the expandable anchor, at a distal end of the expandable anchor, or both.

In some embodiments, the expandable anchor includes a self-expandable stent or scaffold. In some embodiments, the blood impermeable wall includes a blood impermeable covering disposed on at least one of an interior surface and an exterior surface of the expandable anchor and surrounding the adjustable blood flow path.

Some embodiments also include an anchor collapse control element supported by the catheter and adapted to reduce a dimension of the expandable anchor to facilitate placement of the expandable anchor in a sheath. The anchor collapse control element may be supported by the catheter outside of the adjustable blood flow path. Some embodiments may also include an anchor collapse actuator disposed at a proximal section of the catheter and adapted to actuate the anchor collapse control element. The anchor collapse control element may be adapted to reduce a cross-sectional dimension of a proximal end of the expandable anchor. In some embodiments, the anchor collapse control element includes a line slidingly disposed in a plurality of loops on the proximal end of the expandable anchor and extending proximally through a lumen of the catheter, and the loops may optionally be integral with the expandable anchor. Some embodiments also include a second anchor collapse control element supported by the catheter and adapted to reduce a cross-sectional dimension of a distal end of the expandable anchor. The second anchor collapse control element may be supported by the catheter outside of the adjustable blood flow path.

Some embodiments of the invention also include a first pressure sensor adapted to measure a pressure distal to the adjustable blood flow path and a second pressure sensor adapted to measure a pressure proximal to the adjustable blood flow path. Some such embodiments may also have a pressure port disposed on the catheter distal to the adjustable blood flow path and a lumen extending from the pressure port through the catheter to the first pressure sensor and/or a pressure port disposed on the catheter proximal to the adjustable blood flow path and a lumen extending from the pressure port through the catheter to the second pressure sensor. In some embodiments, the first pressure sensor may be supported by the catheter distal to the distal opening of the adjustable blood flow path, and the second pressure sensor is supported by the catheter proximal to the proximal opening of the adjustable blood flow path. Some embodiments also include a processor configured to operate the blood flow control actuator to actuate the flow control element based on pressures sensed by the first pressure sensor and the second pressure sensor.

Another aspect of the invention provides a method of controlling a blood flow rate in a blood vessel. In some embodiments, the method includes the steps of advancing a catheter and an expandable anchor into the blood vessel; expanding the anchor in the blood vessel into contact with an inner wall of the blood vessel, the anchor having a blood impermeable wall defining an adjustable blood flow path extending through the anchor from a proximal opening to a distal opening, the catheter being disposed outside of the adjustable blood flow path; allowing blood to flow from the blood vessel into the adjustable blood flow path through the anchor; and changing a dimension of the adjustable blood flow path, thereby changing a rate of blood flow through the adjustable blood flow path.

In some embodiments, the step of changing a dimension of the adjustable blood flow path includes the step of changing a shape of the anchor by, e.g., compressing a self-expandable portion of the anchor and/or releasing a compression force on a self-expandable portion of the anchor.

The step of changing the shape of the anchor could also include the step of actuating a flow control element to change a force applied to the blood flow control device, the flow control element being disposed outside of the adjustable blood flow path. In some embodiments, the flow control element includes a cinching line supported by the catheter outside of the adjustable blood flow path extending proximally from the anchor, and the step of actuating the flow control element includes the step of changing a cinching force applied to the anchor by the cinching line. The cinching line may optionally engage a central portion of the anchor, and the step of changing the shape of the anchor may then include the step of changing a shape of the central portion. Alternatively or additionally, the cinching line may optionally engage a distal portion of the anchor, and the step of changing the shape of the anchor may include the step of changing a shape of the distal portion. Alternatively or additionally, the cinching line may optionally engage a proximal portion of the anchor, and the step of changing the shape of the anchor may include the step of changing a shape of the proximal portion.

In embodiments in which the anchor includes a self-expandable scaffold or stent, the advancing step may include the step of advancing the catheter within a delivery sheath, and the expanding step may include the step of moving the catheter and the delivery sheath with respect to each other to allow the scaffold to self-expand. Some such embodiments may also include the step of collapsing the anchor and disposing the delivery sheath around the anchor. The step of collapsing the anchor may also include the step of compressing a proximal end of the anchor prior to disposing the delivery sheath around the anchor. The step of collapsing the anchor may also include the step of compressing a distal end of the anchor. The step of collapsing the anchor may also include the step of actuating an anchor collapse control element, and the anchor collapse control element may optionally be supported by the catheter outside of the adjustable blood flow path.

Some embodiments also include the steps of measuring a first pressure in the blood vessel proximal to the anchor and a second pressure in the blood vessel distal to the anchor and changing a dimension of the adjustable blood flow path based on difference between the first pressure and the second pressure. In some embodiments, the step of expanding the anchor may include the step of moving an end of the anchor longitudinally with respect to the catheter.

Yet another aspect of the invention provides a blood flow control device having a catheter adapted to be advanced into a blood vessel to a blood flow control site within the blood vessel; and an expandable anchor supported by the catheter, the expandable anchor being adapted to expand to engage a wall of the blood vessel, the expandable anchor having a blood impermeable wall defining a blood flow path extending through the expandable anchor from a proximal opening to a distal opening and a reduced flow area portion in the blood flow path, the catheter being disposed outside of the blood flow path.

In some embodiments, the reduced flow area portion of the expandable anchor is disposed at the distal opening such that the distal opening has a smaller open area than an open area of the proximal opening. In some embodiments, the reduced flow area portion of the expandable anchor is disposed between the proximal opening and the distal opening.

In some embodiments, the expandable anchor is disposed on an exterior side of the catheter at a distal section of the catheter such that the catheter is outside of the anchor. Some embodiments also include a sliding connector between the expandable anchor and the catheter adapted to permit at least one end of the expandable anchor to move longitudinally with respect to the catheter when the expandable anchor expands or collapses. The sliding connector may be disposed at a proximal end and/or at a distal end of the expandable anchor.

In some embodiments, the expandable anchor has a self-expandable scaffold. In some embodiments, the blood impermeable wall includes a blood impermeable covering disposed on at least one of an interior surface and an exterior surface of the expandable anchor and surrounding the adjustable blood flow path.

Some embodiments include an anchor collapse control element supported by the catheter and adapted to reduce a dimension of the expandable anchor to facilitate placement of the expandable anchor in a sheath. The anchor collapse control element may be supported by the catheter outside of the adjustable blood flow path. Some embodiments may also include an anchor collapse actuator disposed at a proximal section of the catheter and adapted to actuate the anchor collapse control element. In some embodiments, the anchor collapse control element is adapted to reduce a cross-sectional dimension of a proximal end of the expandable anchor. The anchor collapse control element may include a line slidingly disposed in a plurality of loops on the proximal end of the expandable anchor and extending proximally through a lumen of the catheter, and the loops optionally be integral with the expandable anchor.

Still another aspect of the invention provides a method of reducing a blood flow rate in a blood vessel. In some embodiments, the method includes the steps of advancing a catheter and an expandable anchor into the blood vessel; expanding the anchor in the blood vessel into contact with an inner wall of the blood vessel, the anchor having a blood impermeable wall defining a blood flow path extending through the anchor from a proximal opening to a distal opening and a reduced flow area portion in the blood flow path, the catheter being disposed outside of the adjustable blood flow path; and allowing blood to flow from the blood vessel into the proximal opening and through the blood flow path and the distal opening, thereby reducing the blood flow rate in the blood vessel.

In some embodiments, the reduced flow area portion of the expandable anchor is disposed at the distal opening such that the distal opening has a smaller open area than an open area of the proximal opening. In some embodiments, the reduced flow area portion of the expandable anchor is disposed between the proximal opening and the distal opening.

In some embodiments, the anchor includes a self-expandable scaffold, and the advancing step includes the step of advancing the catheter within a delivery sheath, the expanding step including the step of moving the catheter and the delivery sheath with respect to each other to allow the scaffold to self-expand. Some embodiments also include the steps of collapsing the anchor and disposing the delivery sheath around the anchor. Some embodiments also include the step of compressing a proximal end of the anchor prior to disposing the delivery sheath around the anchor. The step of collapsing the anchor may include the step of actuating an anchor collapse control element. The anchor collapse control element may be supported by the catheter outside of the adjustable blood flow path.

Some embodiments include the step of measuring a first pressure in the blood vessel proximal to the anchor and a second pressure in the blood vessel distal to the anchor. In some embodiments, the expanding step includes the step of moving an end of the anchor longitudinally with respect to the catheter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Described herein are catheter-based blood flow occlusion devices that can be placed either in the SVC to decrease blood flow returning from the head and upper extremities or placed in the IVC in an infrarenal location in order to decrease blood flow returning from the lower extremities. The devices can restrict blood flowing in the antegrade direction, resulting in a higher pressure on the inflow (proximal) side and a lower pressure on the outflow side, distal to the device.

Figure 1:
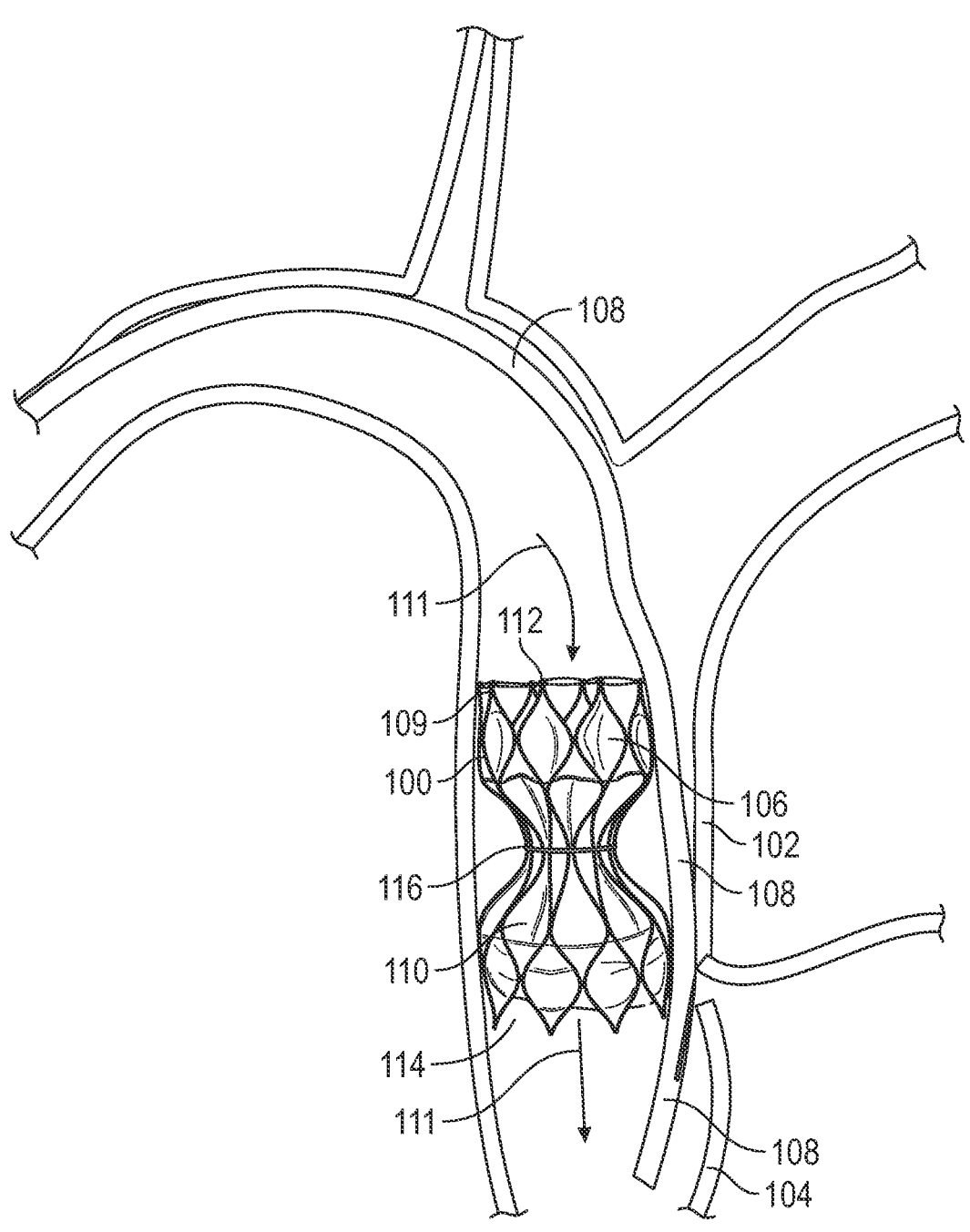
FIG. 1 shows an exemplary blood flow control device located in the SVC.

For example, FIG. 1 shows an exemplary blood flow control device 100 disposed in the SVC 102 above the right atrium 104 of the patient's heart. Device 100 has an expandable anchor 106 supported by a catheter 108. Anchor 106 expands to engage the inside wall of the blood vessel (e.g., the SVC). In the illustrated embodiment, anchor 106 has a scaffold formed as a self-expandable stent 109 covered by a blood impermeable covering 110 to define a blood flow path (illustrated by arrows 111) extending from proximal opening 112 to and through a distal opening 114. A reduced diameter portion 116 of the anchor creates at least a partial occlusion to blood flow through the device by reducing the area through which the blood is flowing.

Figure 2:
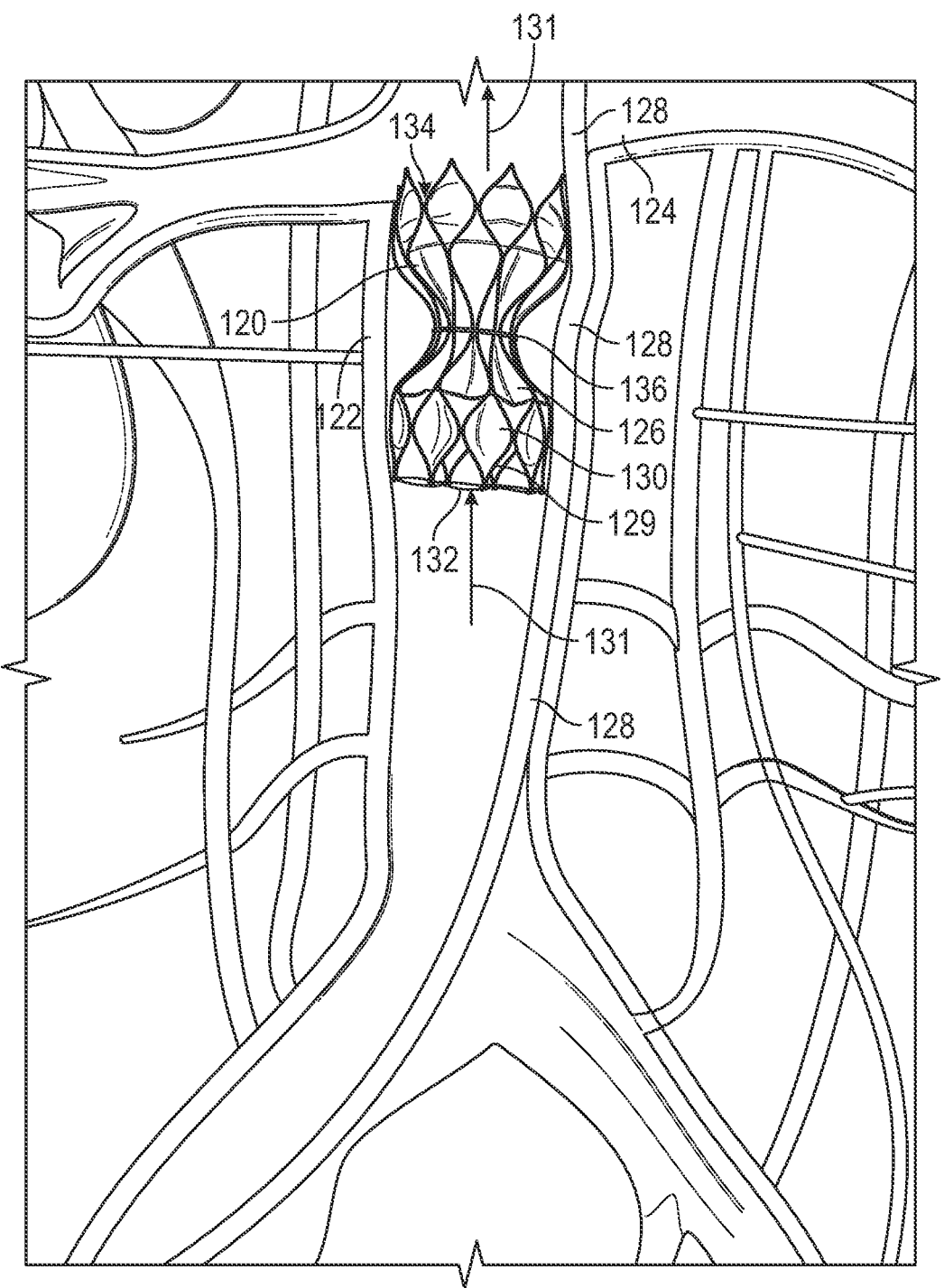
FIG. 2 shows an exemplary blood flow control device located in the IVC.

FIG. 2 shows a blood flow control device 120 similar to that of FIG. 1 in the IVC 122, e.g., just below the renal veins 124. As in device 100, device 120 has an expandable anchor 126 supported by a catheter 128. Anchor 126 expands to engage the inside wall of the blood vessel (e.g., the SVC). In the illustrated embodiment, anchor 126 has a scaffold formed as a self-expandable stent 129 covered by a blood impermeable covering 130 to define a blood flow path (illustrated by arrows 131) extending from proximal opening 132 to and through a distal opening 134. A reduced diameter portion 136 of the anchor creates at least a partial occlusion to blood flow through the device by reducing the area through which the blood is flowing.

The blood flow control devices described herein can include an expandable and compressible anchor that, in its expanded state, can accommodate a range of IVC or SVC diameters and seal against the IVC or SVC. In some embodiments, for example, the anchor can have an expanded diameter of 20-30 mm. The blood flow control devices described herein can further be compressible to a small enough diameter to be inserted via an introducer sheath placed in a peripheral vein, for instance inserted into the subclavian vein (for placement in the SVC location) or into the femoral vein (for placement in the IVC location).

The blood flow control devices described herein can have a non-thrombogenic surface on their inside diameter. In some embodiments, the flow occlusion devices can have minimal or no stent wires and/or no catheter shaft within the flow lumen in order to decrease the risk of thrombus forming on the device.

In some embodiments, the blood flow control devices described herein can be cylindrical. In other embodiments, the flow occlusion devices can have a narrowed location along their length in order to decrease the flow rate therethrough.

The blood flow control devices described herein can have a blood flow control element configured to vary the flow rate through the device, such as from fully open to partially or fully closed.

The blood flow control devices described herein can be configured to provide feedback to the physician. For example, the flow occlusion devices described herein can include pressure sensors supported by the catheter on or near the anchor and/or pressure-measuring lumens in the catheter communicating with ports distal and proximal to the device and leading to pressure sensors outside of the patient. As another example, the blood flow control devices described herein can include a flow rate sensor (e.g., within the narrowed location of the device or positioned distally and proximally to the device on the catheter). In some embodiments, the data from the pressure and/or flow sensors can be used by the physician to make adjustments to the blood flow control device to vary the flow rate or pressure differential as desired. In other embodiments, the data from the pressure and/or flow sensors can provide input to a controller, which can then automatically adjust the blood flow control device to vary the flow rate or pressure differential as desired. In some embodiments, other parameters may be used as the basis for adjusting the blood flow control device, such as right atrial pressure, pulmonary pressure, pulmonary capillary wedge pressure, urine output, and the like.

FIGS. 3-10 show aspects of various embodiments of the blood flow control device shown in FIG. 2. A delivery sheath 140 may be used to deliver catheter 128 and anchor 126 to the desired blood flow control location within a blood vessel, such as the IVC 122 shown in FIG. 5. Proximal and distal portions 142 and 144 of anchor 126 self-expand to contact the blood vessel wall and to press catheter 128 against the blood vessel wall. When in place in the blood vessel, blood flows along the blood flow path 131 into a proximal opening 138, through the interior of the anchor and out of a distal opening 139. As seen best in FIGS. 4-5, anchor 126 is supported on an exterior side of catheter 128 at a distal section of the catheter such that the catheter is outside of anchor 126 and therefore outside of the blood flow path 131. Disposition of the catheter outside of the blood flow path may reduce clotting and hemolysis during use of the blood flow control device.

Figure 3:
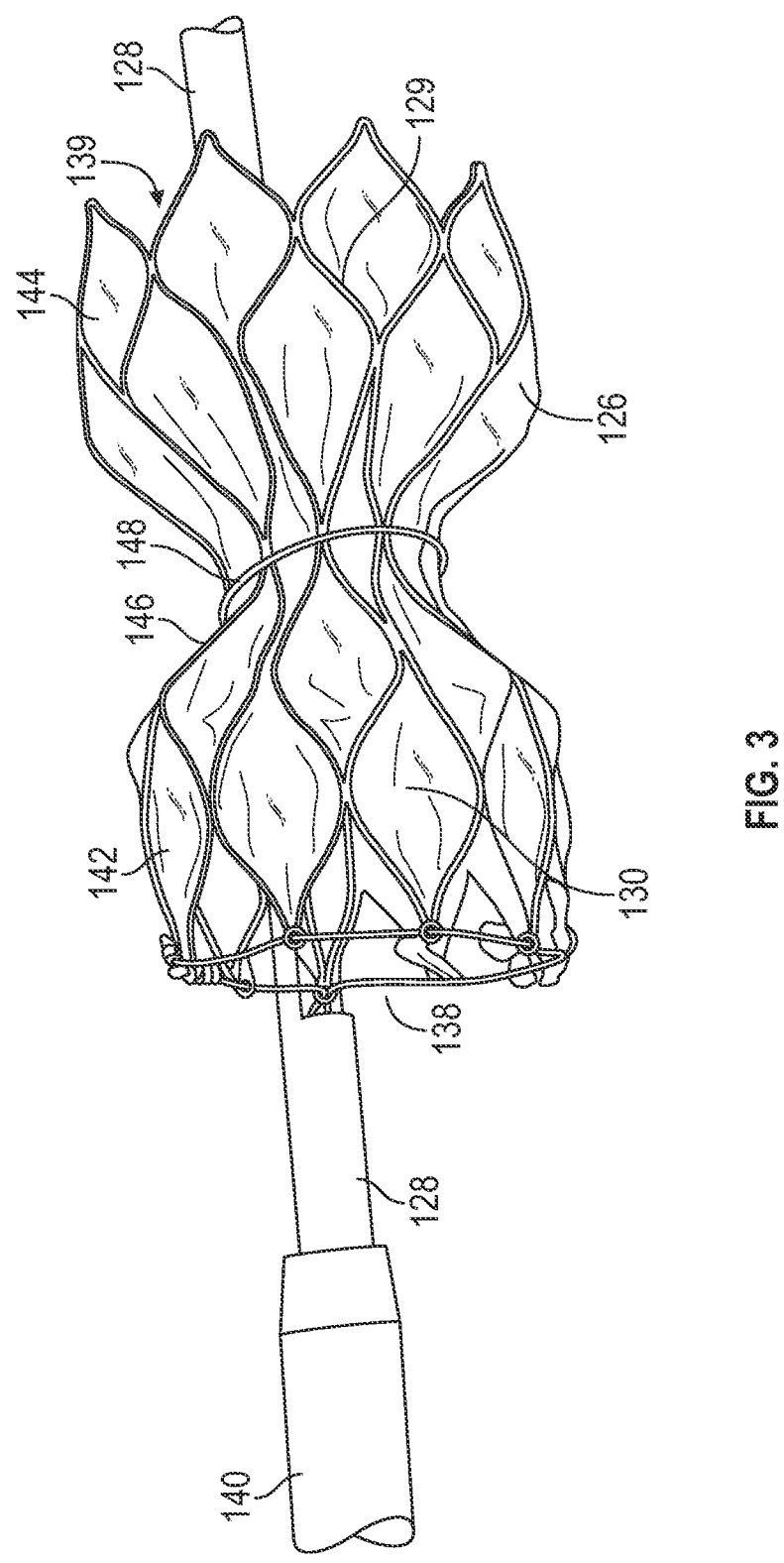
FIG. 3 is a perspective view of the blood flow control device shown in FIG. 2 in an expanded configuration.
Figure 4:
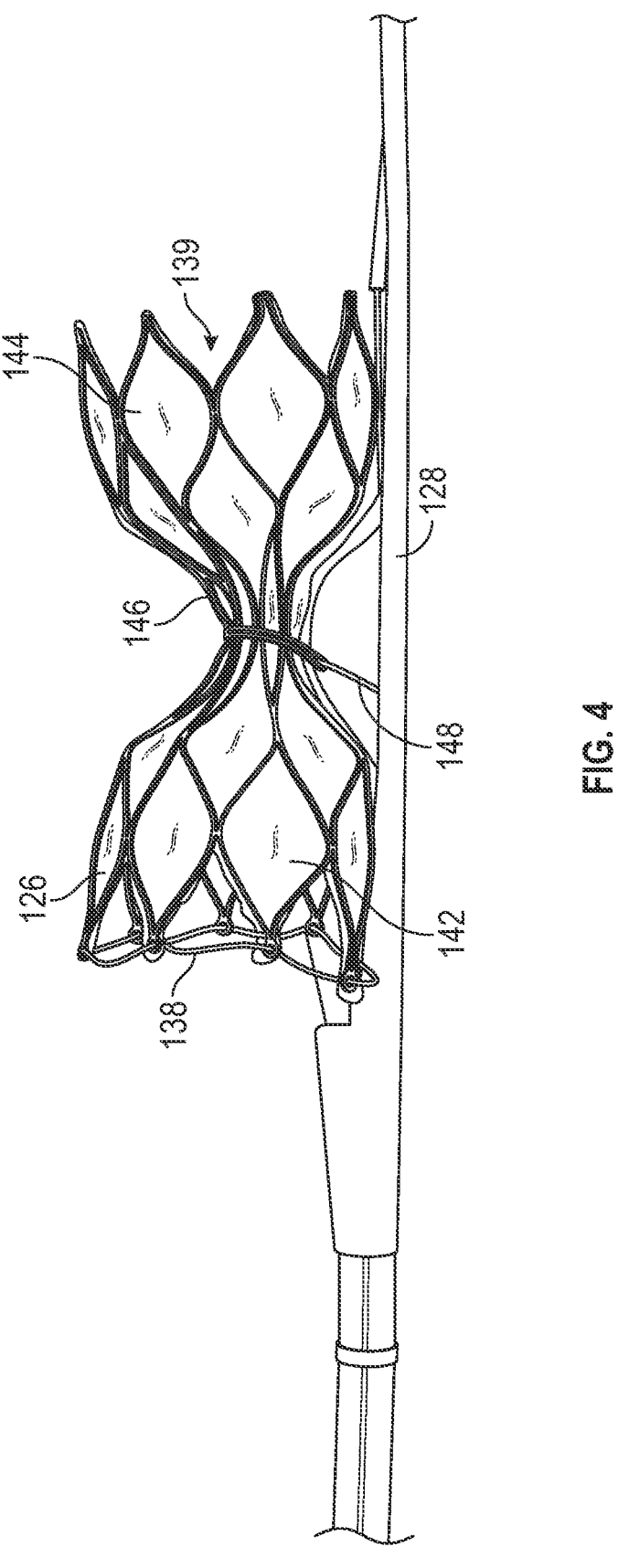
FIG. 4 is a perspective view of the blood flow control device of FIG. 3 in a cinched configuration to change the blood flow path.
Figure 5:
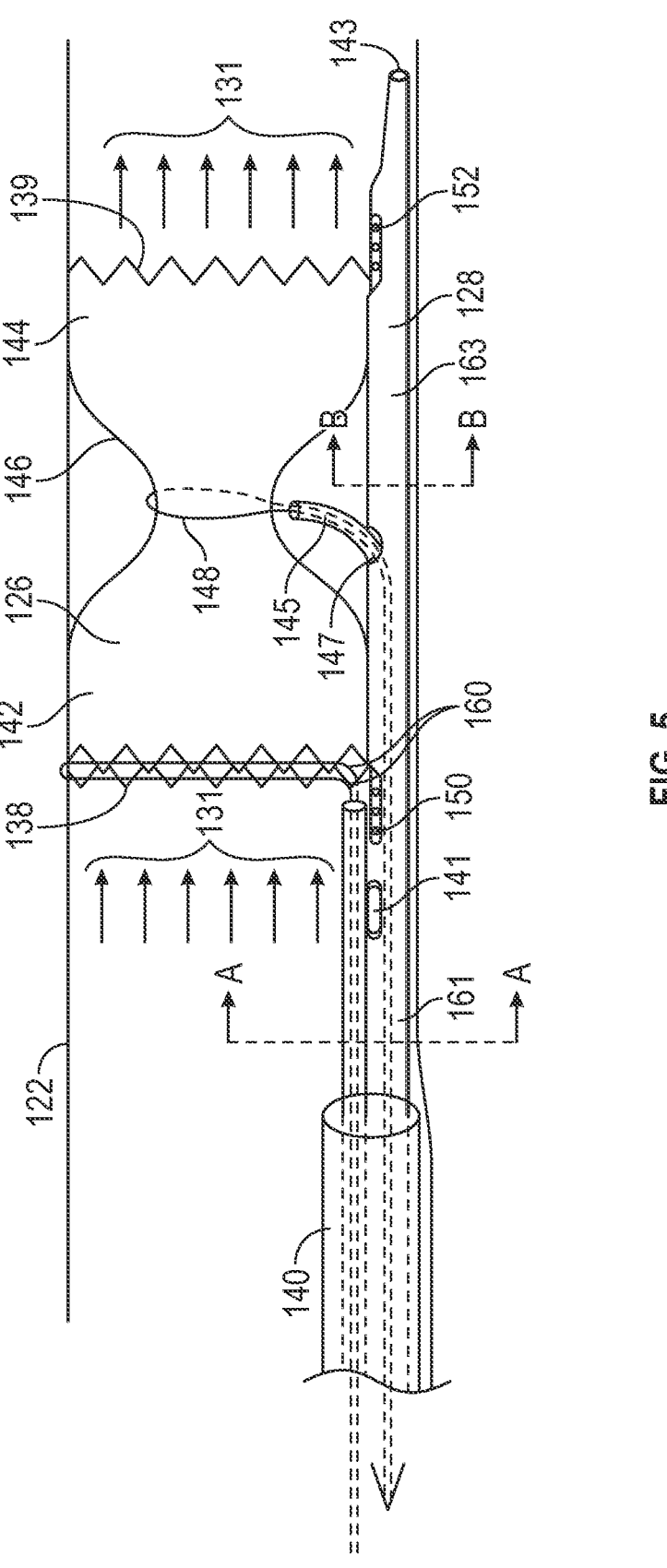
FIG. 5 is a side schematic view of the blood flow control device of FIG. 3.
Figures 6D, 7, 8:
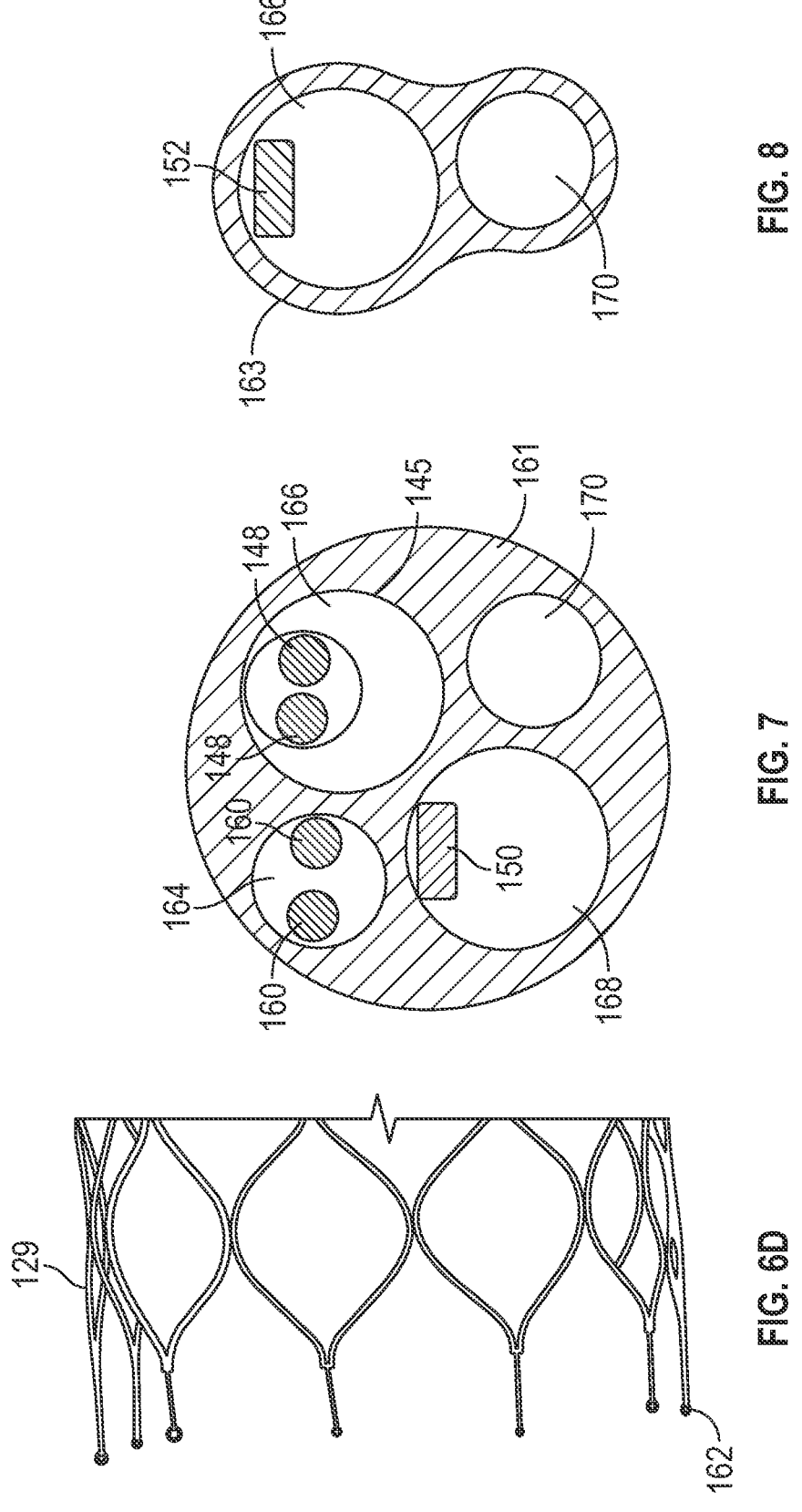
FIG. 6D is a perspective view of a proximal portion of the stent of FIGS. 6A-C.
FIG. 7 is a cross-sectional view of the catheter of the blood flow control device of FIG. 5 taken along the line A-A.
FIG. 8 is a cross-sectional view of the catheter of the blood flow control device of FIG. 5 taken along the line B-B.

In this embodiment, the blood flow control device can be adjusted to change a dimension of the blood flow path and the amount of occlusion the device provides. The blood flow path through the device is therefore an adjustable blood flow path. A central waist portion 146 of anchor 126 self-expands to a diameter smaller than the diameters of proximal and distal portions 142 and 144, as shown in FIGS. 3 and 5. A flexible cinch line 148 (e.g., suture material, such as a braided or monofilament polymer fiber, or a flexible wire or cable) encircles the waist portion 146 to serve as an actuatable flow control element. In one embodiment, a loop of the cinch line 148 wraps around waist portion 146, and the two free ends of the cinch line 148 pass through the loop and extend proximally from anchor 126 into a lumen 166 of catheter 128, as shown in FIG. 7. When the two free ends are pulled proximally (e.g., under the control of an actuator at the proximal end of the catheter), cinch line 148 cinches and changes a dimension of the waist portion 146 to change the shape, and reduce the area, of the anchor and of the adjustable blood flow path at that point, as shown in FIG. 4. Reduction of blood flow through the blood vessel lowers blood pressure downstream of the blood flow control device. Release of the flow control element 148 allows the waist portion 146 of anchor 126 to return to its unconstrained shape, shown in FIGS. 3 and 5.

In this embodiment, the two portions of the cinch line 148 are optionally disposed in a tube 145 which extends out of a port 147 on catheter 128. Tube 145 and the two parts of cinch line 148 extend proximally through a lumen 166 of catheter 128 to an actuator (e.g., the actuator 1300 shown in FIG. 27) at the proximal end of catheter 128, outside of the patient. Tube 145 may be omitted in other embodiments. As shown, the flow control element is supported by the catheter out of the adjustable blood flow path.

The blood flow control device of this invention may be used to lower blood pressure within a blood vessel, e.g., in the SVC or in the IVC. Lowering blood pressure in the SVC or in the IVC may also lower pressure in the right side of the patient's heart and may be beneficial in treating heart failure. Pressure sensors may be used to determine the amount of blood pressure reduction achieved by the device. In the embodiment shown in FIGS. 3-8, a port 141 on catheter 128 proximal to anchor 126 may communicate blood pressure at that point via a lumen 168 (shown in FIG. 7) in the catheter to a first pressure sensor (not shown) on the proximal end of catheter 128. Likewise, a port 143 at the distal end of catheter 128 may communicate via a lumen 170 (shown in FIGS. 7 and 8) in the catheter to a second pressure sensor (not shown) on the proximal end of catheter 128. Lumen 170 may also be used as a guidewire lumen for delivery of blood flow control device 120 to the desired site in the blood vessel.

Figure 6A:
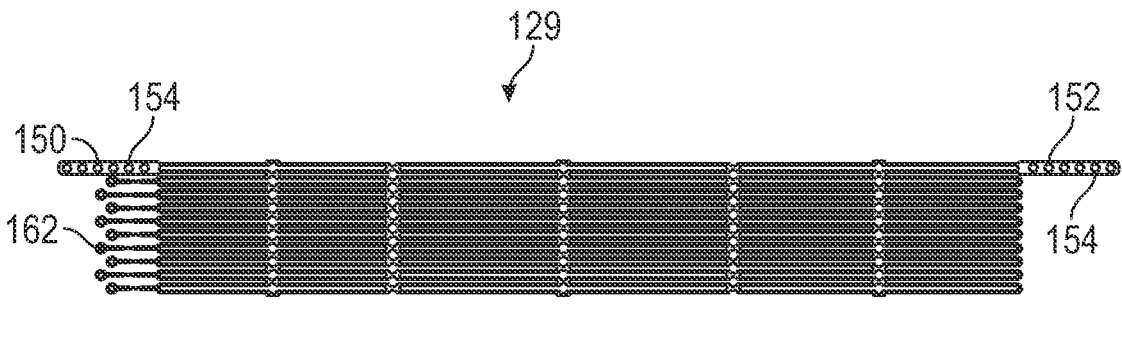
FIG. 6A is a flat plan of a stent serving as a scaffold in the anchor of the blood flow control device of FIG. 3.
Figure 6B:
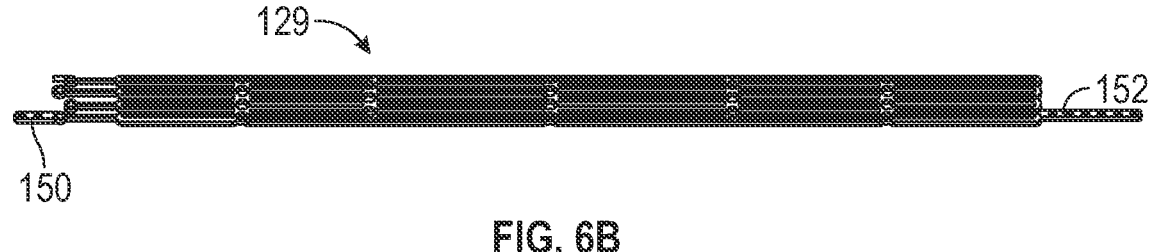
FIG. 6B is a side view of the stent of FIG. 6A in a compressed configuration.
Figure 6C:
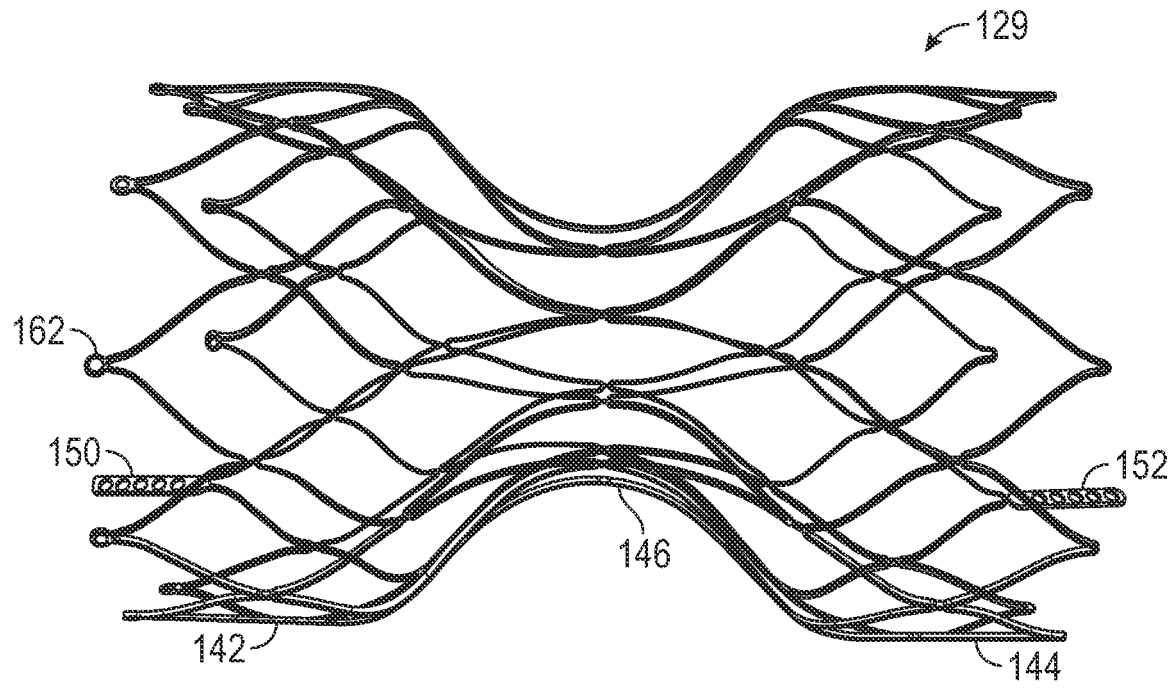
FIG. 6C is a perspective view of the stent of FIGS. 6A and 6B in an expanded configuration.

FIGS. 6A-D show details of a stent 129 that may serve as the scaffold of anchor 126. Stent 129 may be formed from a shape memory material such as Nitinol. FIG. 6A shows a flat pattern to be used to cut stent 129 out of a solid tube, FIG. 6B shows the cut tube prior art being heat set into to the shape shown in FIG. 6C with the larger diameter proximal and distal portions 142 and 144 and the smaller diameter waist portion 146.

Figure 9A:
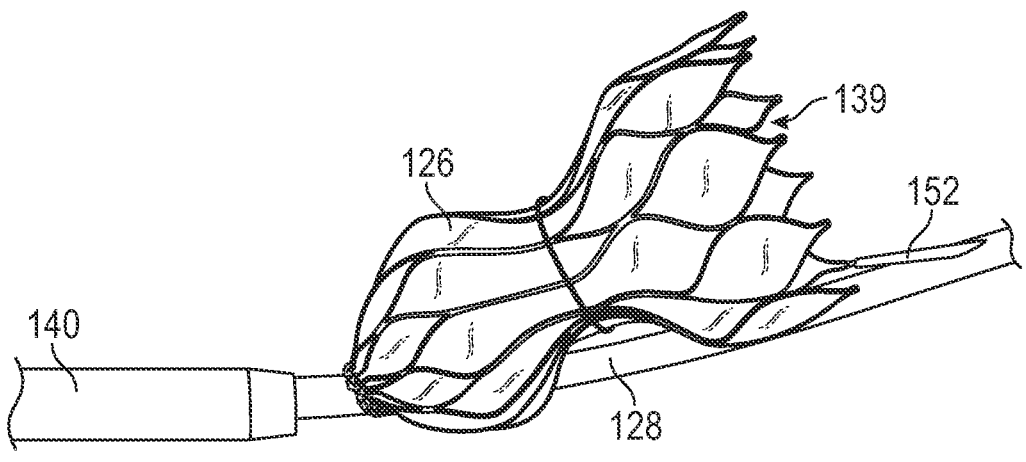
FIG. 9A is a perspective view showing the collapse of the proximal end of the anchor of the blood flow control device of FIG. 3 prior to retrieval into a delivery sheath.
Figure 9B:
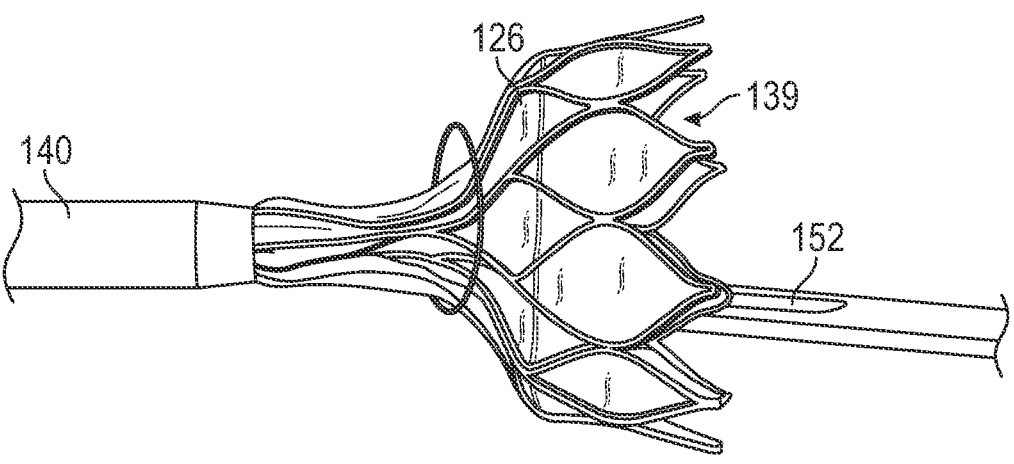
FIG. 9B is a perspective view showing retrieval of the anchor of the blood flow control device of FIG. 3 into the delivery sheath.
Figure 10:
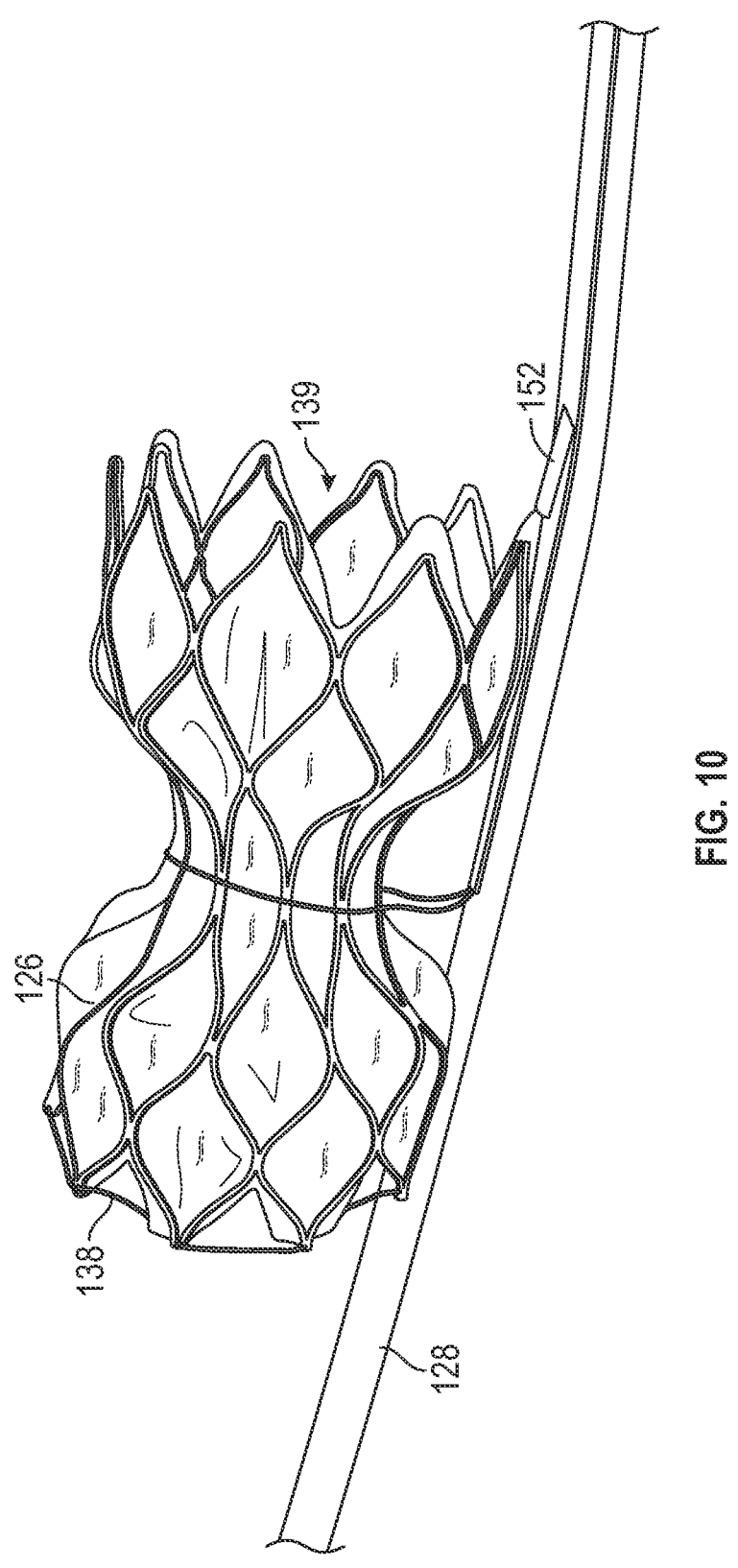
FIG. 10 is a perspective view of the blood flow control device of FIG. 3.

Proximal and distal catheter attachment elements 150 and 152 may be formed on the proximal and distal ends of stent 129. In some embodiments, one or both of the catheter attachment elements may be slidingly disposed in a lumen of catheter 128 so that the one or both ends of the stent can move with respect to the catheter as the stent expands or is compressed. Instead of sliding in a lumen of the catheter, one of the attachment elements may be fixed to the catheter by employing the holes 154 for the application of adhesive or for polymer melt bonding in a lumen of the catheter or on an outside surface of the catheter. For example, proximal catheter attachment element 150 may be slidingly disposed in lumen 168 of catheter 128, as shown in FIG. 7, and distal catheter attachment element 152 may be fixedly attached to the interior of lumen 166 of catheter 128, as shown in FIG. 8. Alternatively, distal catheter attachment element 152 may be slidingly disposed in lumen 166, as shown in FIGS. 9A-B and 10, and the proximal catheter attachment element 150 may be either fixedly or slidingly disposed in lumen 168. In yet another alternative embodiment, the proximal and/or distal attachment element may be bonded to a tube, and the tube may be slidingly disposed in a lumen of the catheter. A blood impermeable covering 130 may be applied to the outer and/or inner surfaces of stent 129.

Some embodiments of the invention provide an anchor collapse control element to facilitate collapse of the anchor and placement of the collapsed anchor within the delivery sheath. In the embodiments shown in FIGS. 3-10, a collapsing line 160 threaded through the proximal end of stent 129 serves as an anchor collapse control element. The two sides of collapsing line 160 extend through a lumen 164 of catheter 128 where its two ends can be drawn proximally to collapse the proximal end of anchor 126 and draw it toward lumen 164, as shown in FIG. 9A, at which point the catheter 128 and anchor 126 can be drawn into the delivery sheath 140, as shown in FIG. 9B. Collapsing line 160 may be, e.g., a polymer fiber (monofilament or braided polymer line) or a flexible metal wire or cable. Alternatively or additionally, a collapsing line may be attached to the distal end of the anchor to assist with compression of the device when retracting into the delivery sheath.

Collapsing line 160 may be threaded through eyelets 162 formed in stent 129. Eyelets may be turned 90° during heat set of stent 129, as shown in FIG. 6D. Alternatively, the collapsing line may be threaded directly through the proximal stent cells. As yet another alternative, small metal or polymer loops may be attached to the proximal stent cells, and the collapsing line may be threaded through the loops. In embodiments of the invention, the anchor collapse control element is supported by the catheter outside of the adjustable blood flow path.

FIG. 7 is a cross-section of catheter 128 along line A-A in FIG. 5, and FIG. 8 is a cross-section of catheter 128 along line B-B in FIG. 5. Catheter 128 has a four lumen proximal section 161 and a two lumen distal section 163. In some embodiments, distal section 163 may be formed separately from proximal section 161, and the two sections may be bonded end to end to line up lumens 166 and 170. Lumens 164 and 168 terminate prior to the proximal end of distal section 163.

Figure 11:
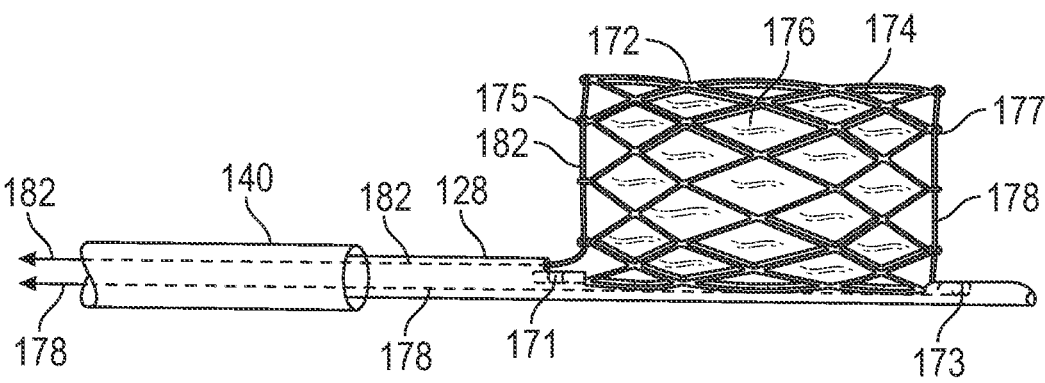
FIG. 11 is a side view of another embodiment of a blood flow control device.
Figure 12:
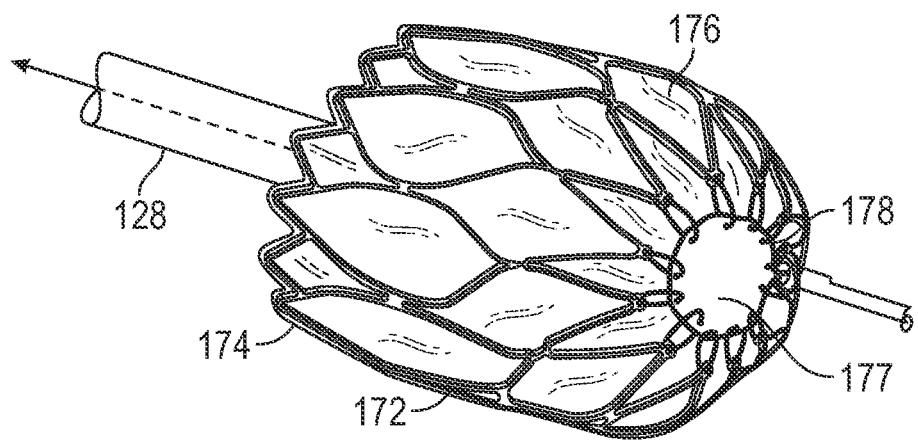
FIG. 12 is a perspective view of the blood flow control device of FIG. 11 showing a reduced distal opening.
Figure 13:
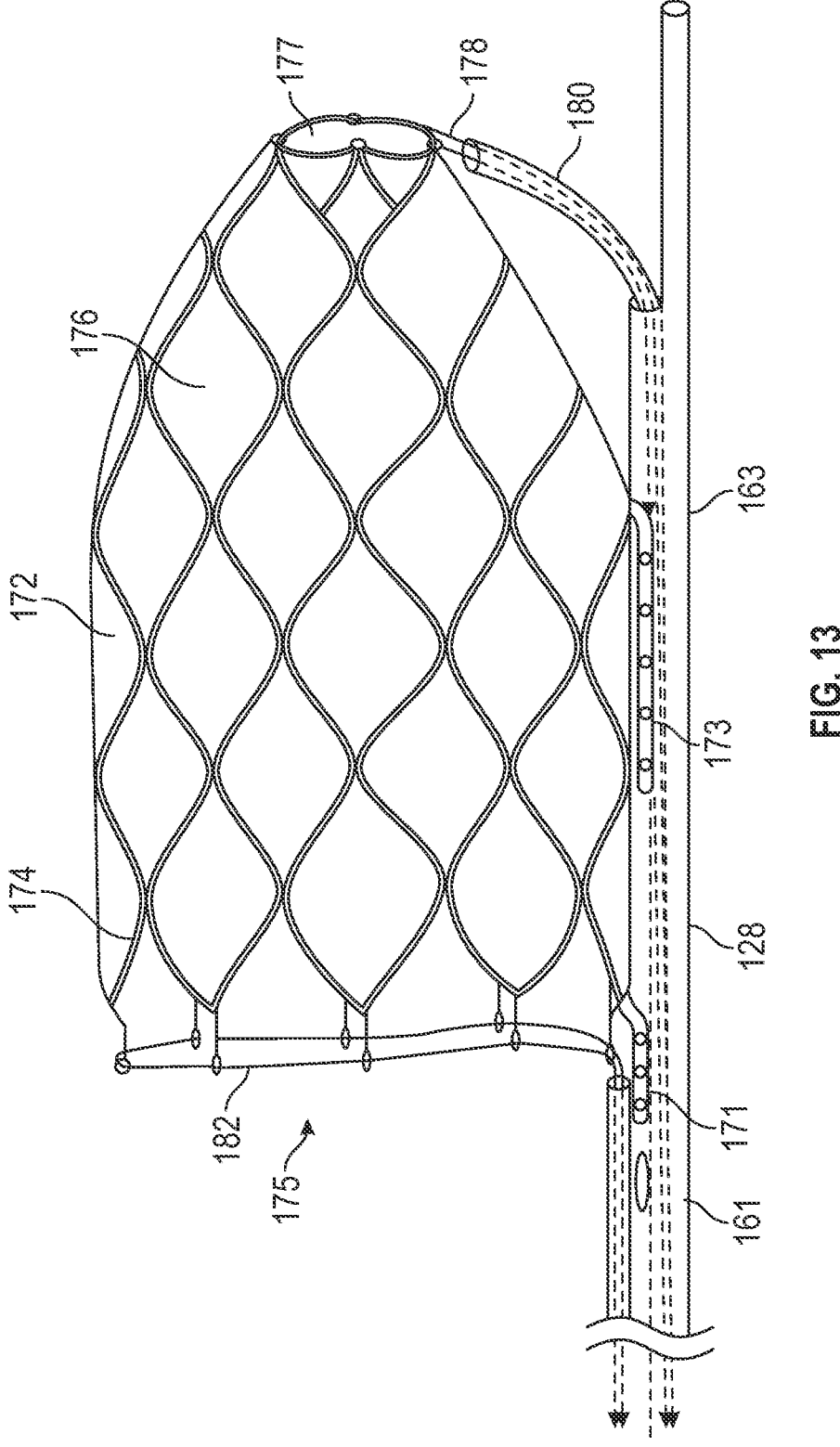
FIG. 13 is a perspective view of yet another embodiment of a blood flow control device.

FIGS. 11-13 show other embodiments of the blood flow control device of this invention. Like the embodiments of FIGS. 3-10, the device has a catheter 128 having four lumens in a proximal section 161 and two lumens in a distal section 163. The anchors have different shapes, however. In the embodiment shown in FIGS. 11 and 12, the anchor 172 of has an uncompressed shape of a cylinder, not an hourglass. In the embodiment shown in FIG. 13, the anchor 172 has an uncompressed shape that has a larger diameter on its proximal and central portions and a smaller diameter at its distal end. As in the earlier embodiments, in both of these embodiments anchor 172 has a stent 174 that may serve as the scaffold of anchor 172, and stent 174 may be covered on the outside and/or on the inside by a blood impermeable material 176. Stent 174 may be formed from a shape memory material such as Nitinol. Stent 174 may be attached to catheter 128 via proximal and distal catheter attachment elements 171 and 173, as described above with respect to the embodiments of FIGS. 3-10. These embodiments may also employ lumens within catheter 128 to communicate between pressure ports on the catheter proximal and distal to anchor 172 and pressure sensors at the proximal end of catheter 128. When in place in the blood vessel, anchor 172 expands to engage the inside wall of the blood vessel (e.g., the IVC or the SVC), and blood flows along a blood flow path into a proximal opening 175, through the interior of the anchor and out of a distal opening 177.

A flow control element formed by a flexible cinch line 178 (e.g., suture material, such as a braided or monofilament polymer fiber, or a flexible wire or cable) is slidingly attached to the distal end of stent 174 (e.g., through loops formed in, or attached to, the distal ends of the distal cells of stent 174), and the two free ends of the cinch line 178 extend proximally from anchor 172 into a lumen of catheter 128, as shown in FIGS. 11 and 13. When the two free ends are pulled proximally (e.g., under the control of an actuator at the proximal end of the catheter), cinch line 178 cinches and changes a dimension of the distal end of anchor 172 to change the shape, and reduce the area, of the anchor and of the adjustable blood flow path at that point, as shown in FIGS. 12 and 13. Cinch line 178 may optionally be disposed in a flexible tube 180, and flexible tube 180 may reside within the catheter lumen. Tube 180 and the two parts of cinch line 178 extend proximally through a lumen of catheter 128 to an actuator (e.g., the actuator 1300 shown in FIG. 27) at the proximal end of catheter 128, outside of the patient. Reduction of blood flow through the flow control device lowers blood pressure downstream of the blood flow control device. Release of the flow control element 178 allows anchor 172 to return to its unconstrained shape, shown in FIG. 11. In embodiments of the invention, the flow control element is supported by the catheter outside of the adjustable blood flow path.

The embodiments of FIGS. 11-13 also employ an anchor collapse control element to facilitate collapse of the anchor 172 and placement of the collapsed anchor within the delivery sheath 140. As in the embodiments shown in FIGS. 3-10, a collapsing line 182 threaded through the proximal end of stent 174 (e.g., through loops formed in, or attached to, the proximal ends of the proximal cells of the stent) serves as an anchor collapse control element. The two sides of collapsing line 182 extend through a lumen of catheter 128 where its two ends can be drawn proximally to collapse the proximal end of anchor 172 and draw it into the delivery sheath 140. Collapsing line 182 may be, e.g., a polymer fiber (monofilament or braided polymer line) or a flexible metal wire or cable. In embodiments of the invention, the anchor collapse control element is supported by the catheter outside of the adjustable blood flow path.

Figure 14A:
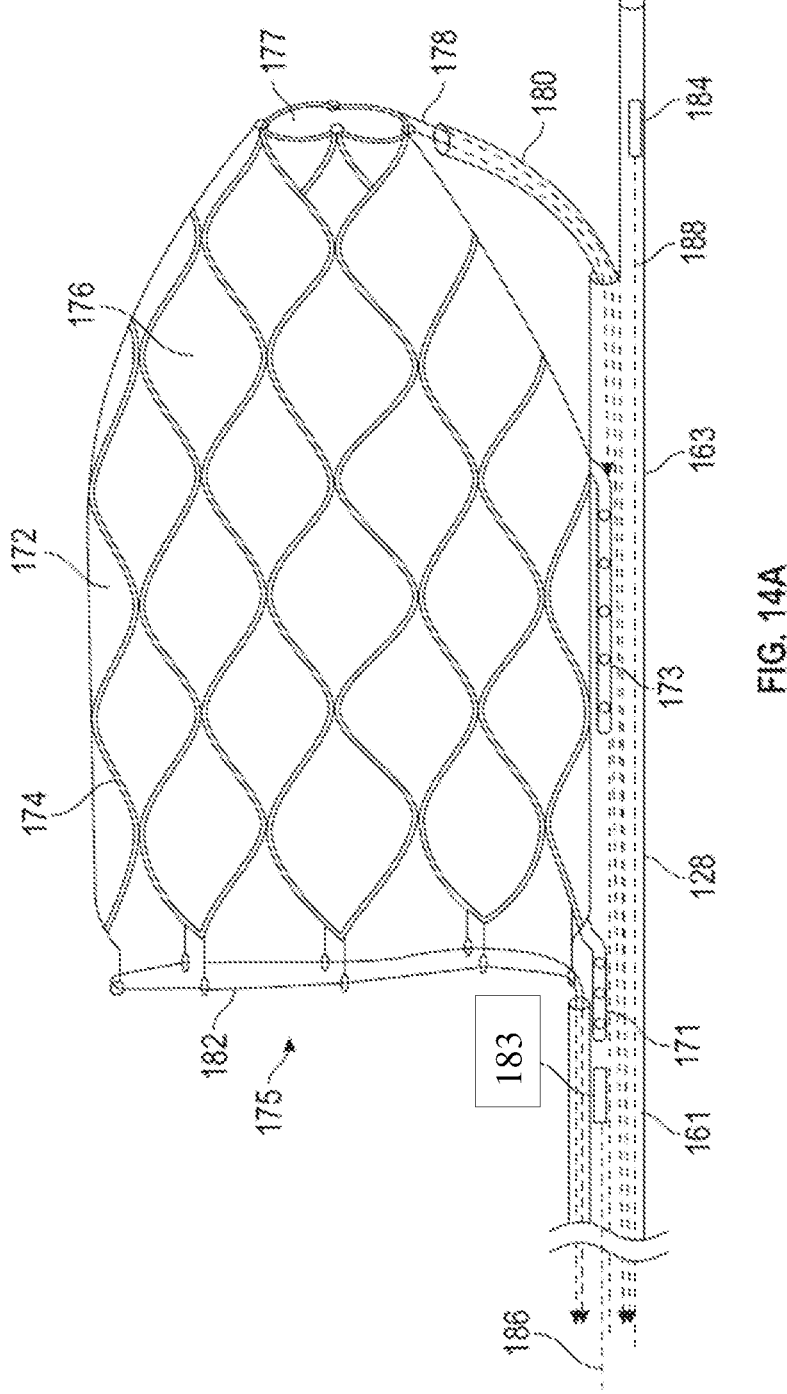
FIG. 14A is a perspective view of still another embodiment of a blood flow control device.

FIG. 14A shows an embodiment of a blood flow control device similar to that of FIGS. 11-13. In this embodiment, however, instead of employing catheter ports and lumens to communicate blood pressure to pressure sensors on the proximal end of the catheter, proximal and distal pressure sensors 183 and 184 are disposed on the catheter proximal and distal to the anchor 172. Conductive wires 186 and 188 extending proximally through the catheter to communicate the outputs of pressure sensors 183 and 184 to a controller (not shown). Pressure sensors 183 and 184 may be MEMS devices or other suitable devices. Such catheter-based pressure sensors may also replace the pressure lumens and proximal pressure sensors of the embodiments of FIGS. 3-10 and other embodiments of the blood flow control device.

Figure 14B:
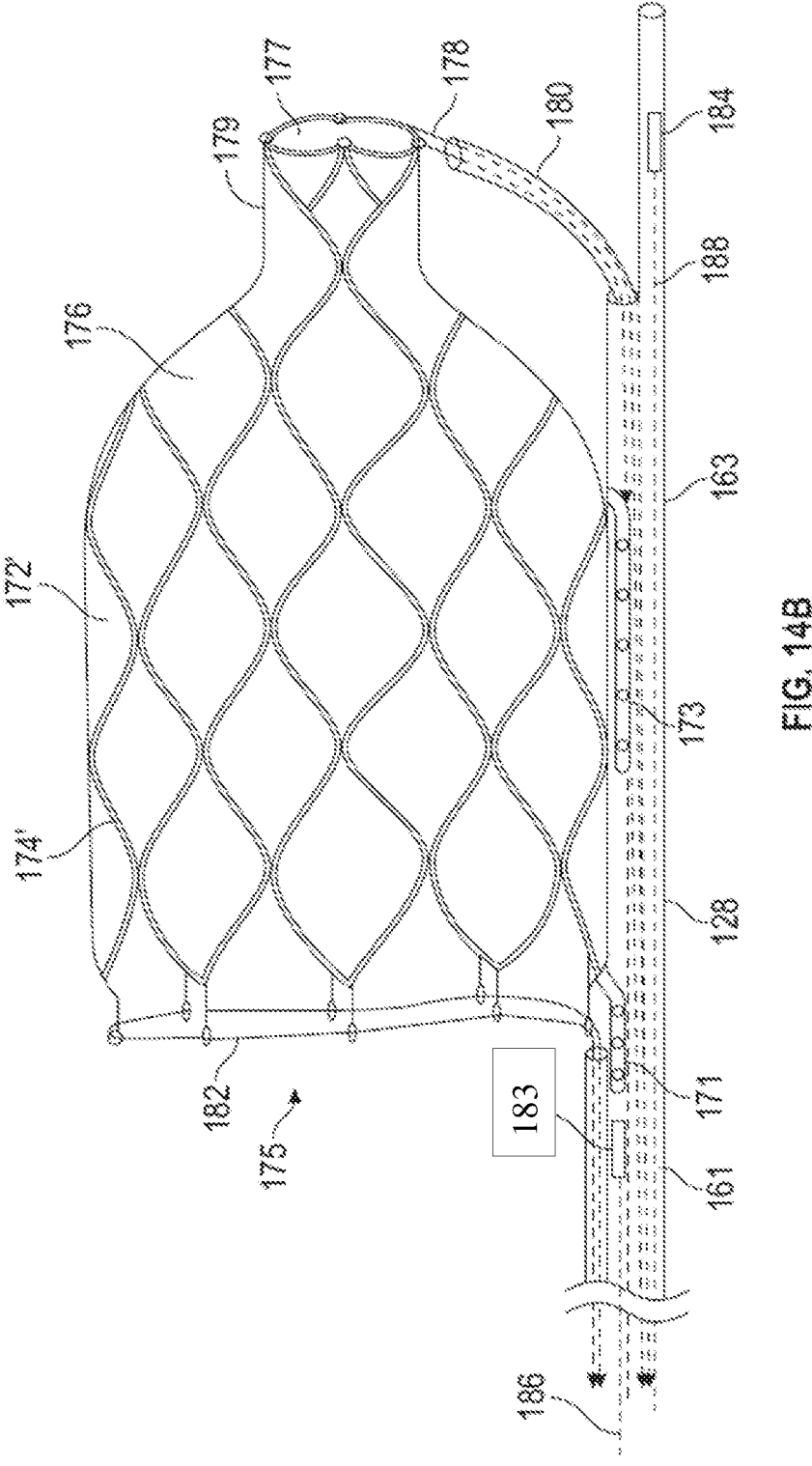
FIG. 14B is a perspective view of another embodiment of a blood flow control device.

FIG. 14B shows an embodiment similar to that of FIG. 14A. Anchor 172', however, has a shape at its distal end that differs from the shape of anchor 172 in FIG. 14A. The stent 174' of anchor 172' is cut and shape set so as to be cylindrical in its distal portion 179 leading up to distal opening 177. This cylindrical shape leading to distal opening 177 may provide a narrower jet of blood, and less turbulent flow, at the outflow end of the blood flow control device.

Figure 15:
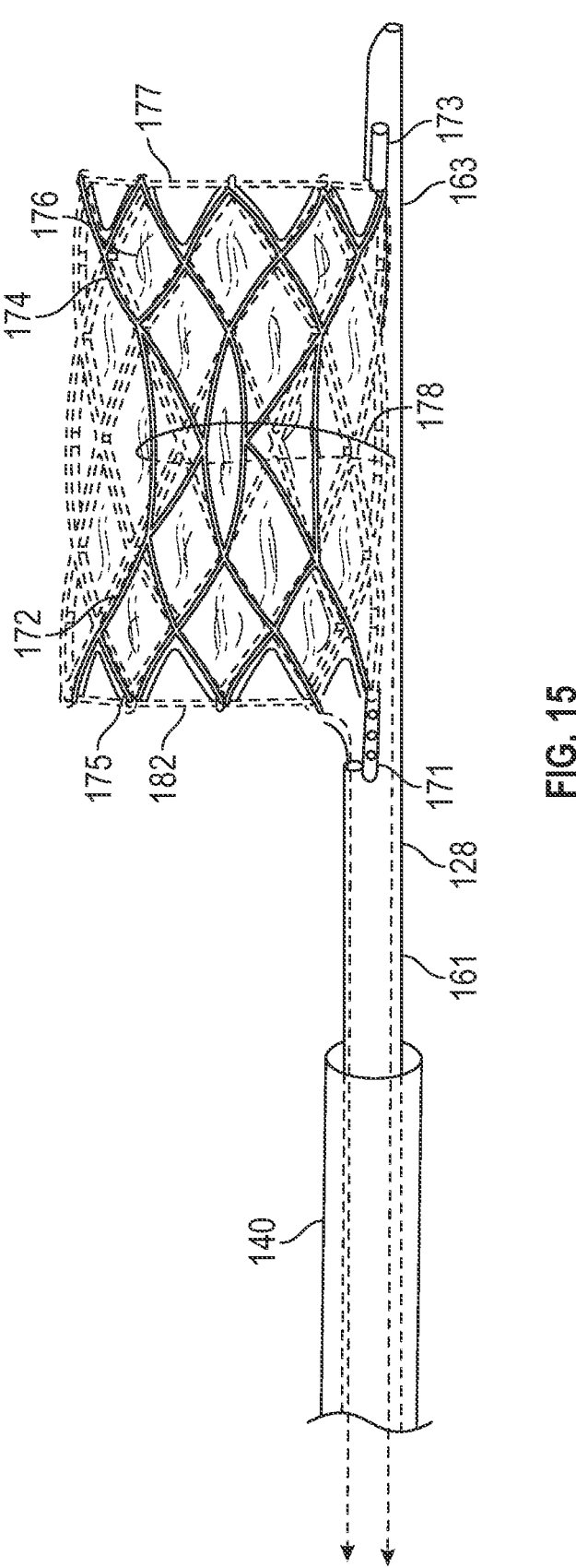
FIG. 15 is a side view of yet another embodiment of a blood flow control device.

FIG. 15 shows an embodiment of a blood flow control device that, like the embodiments of FIGS. 11-13 and FIG. 14, has an anchor 172 which is heat set to be cylindrical in its unconstrained state (shown in phantom in FIG. 15). The device has a catheter 128 having four lumens in a proximal section 161 and two lumens in a distal section 163. As in those earlier embodiments, anchor 172 has a stent 174 that may serve as the scaffold of anchor 172, and stent 174 may be covered on the outside and/or on the inside by a blood impermeable material 176. Stent 174 may be formed from a shape memory material such as Nitinol. Stent 174 may be attached to catheter 128 via proximal and distal catheter attachment elements 171 and 173, as described above with respect to earlier embodiments. This embodiment may also employ lumens within catheter 128 to communicate between pressure ports on the catheter proximal and distal to anchor 172 and pressure sensors at the proximal end of catheter 128. When in place in the blood vessel, anchor 172 expands to engage the inside wall of the blood vessel (e.g., the IVC or the SVC), and blood flows along a blood flow path into a proximal opening 175, through the interior of the anchor and out of a distal opening 177.

A flow control element formed by a flexible cinch line 178 (e.g., suture material, such as a braided or monofilament polymer fiber, or a flexible wire or cable) is slidingly attached to a central portion of anchor 172, and the two free ends of the cinch line 178 extend proximally from anchor 172 into a lumen of catheter 128, as shown in FIG. 15. When the two free ends are pulled proximally (e.g., under the control of an actuator at the proximal end of the catheter, such as actuator 1300 in FIG. 27), cinch line 178 cinches and changes a dimension of the central portion of anchor 172 to change the shape, and reduce the area, of the anchor and of the adjustable blood flow path at that point, as shown in FIG. 15. The two parts of cinch line 178 extend proximally through a lumen of catheter 128 to an actuator (e.g., the actuator 1300 shown in FIG. 27) at the proximal end of catheter 128, outside of the patient. Reduction of blood flow through the blood vessel lowers blood pressure downstream of the blood flow control device. Release of the flow control element 178 allows anchor 172 to return to its unconstrained shape, shown in phantom in FIG. 15. As shown, the flow control element is supported by the catheter outside of the adjustable blood flow path.

The embodiment of FIG. 15 also employs an anchor collapse control element to facilitate collapse of the anchor 172 and placement of the collapsed anchor within the delivery sheath 140. As in the earlier embodiments, a collapsing line 182 threaded through the proximal end of stent 174 (e.g., through loops formed in, or attached to, the proximal ends of the proximal cells of the stent) serves as an anchor collapse control element. The two sides of collapsing line 182 extend through a lumen of catheter 128 where its two ends can be drawn proximally to collapse the proximal end of anchor 172 and draw it into the delivery sheath 140. Collapsing line 182 may be, e.g., a polymer fiber (mono-filament or braided polymer line) or a flexible metal wire or cable. The anchor collapse control element may be supported by the catheter outside of the adjustable blood flow path.

Figure 16:
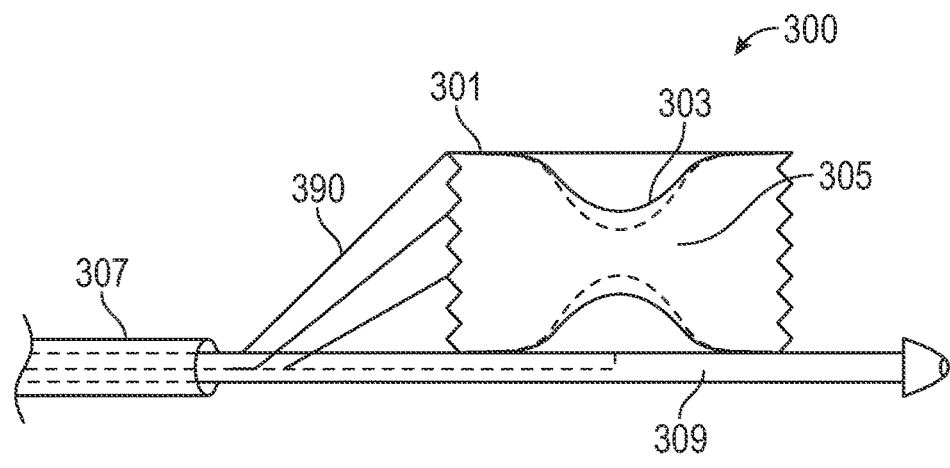
FIG. 16 is a side view of still another embodiment of a blood flow control device.

FIGS. 16-24 illustrate other embodiments of blood flow control devices that provide an adjustable blood flow path. An exemplary blood flow control device 300 is shown in FIG. 16. The blood flow control device 300 includes a cylindrically shaped anchor 301 with a flow channel 305 extending therethrough. The anchor 301 includes a bladder 303 (or otherwise distensible layer) that can be inflated radially inwards, e.g., with a fluid, to cause narrowing or closing of the flow channel 305. The narrowing of the flow channel 305 (and thus the amount of occlusion) can be varied by increasing or decreasing the amount of inflation provided to the bladder 303 (the solid line in FIG. 16 indicates a smaller amount of inflation and the dotted line a larger amount). The anchor 301 is mounted laterally on a catheter 309. Advantageously, the catheter 309 does not extend through the center of the flow channel 305, thereby reducing the chance of thrombus as blood flows through the channel 305. The anchor 301 is configured to be collapsed into the sheath 307 for delivery and expanded (as shown) for use. In one embodiment, the anchor 301 can be configured to self-expand by pulling the sheath 307 proximally. The device 300 can further include a plurality of wires 390 attached to the proximal end thereof and configured to enable collapsing of the anchor 301 into the sheath 307 after use.

Figure 17:
FIG. 17 is a side view of another embodiment of a blood flow control device.

Another exemplary blood flow control device 400 is shown in FIG. 17. The device 400 is similar to device 300 except that the wires 390 are replaced with a single pullwire 421 (e.g., a polymer thread or a metal wire/cable) that wraps through the proximal apexes (i.e., the proximal end) of the anchor 401. To pull the anchor 401 into the sheath 407, the pullwire 421 can be pulled proximally, which can reduce the radius of the proximal end of the anchor 401 for sheathing. Advantageously, the proximal end of the device 400 includes minimal wires within the adjustable blood flow path, thereby reducing the chance of thrombus.

Figure 18:
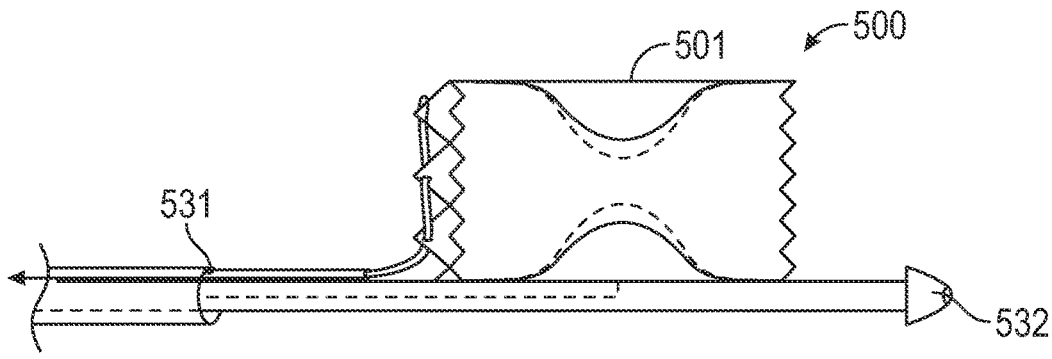
FIG. 18 is a side view of yet another embodiment of a blood flow control device.

Another exemplary blood flow control device 500 is shown in FIG. 18. The device 500 is similar to device 400 except that the device includes a proximal pressure sensor (not shown) and a distal pressure sensor (not shown) disposed at the proximal end of the catheter to enable feedback regarding the amount of occlusion achieved by the device 500. In some embodiments, ports 531 and 532 each communicate with a catheter lumen extending to, and communicating with, the pressure sensors. In other embodiments, pressure sensors may be mounted in the distal portion of the catheter, one proximal to the anchor and one distal to the anchor, as in the embodiment of FIG. 14A. In still other embodiments, the pressure sensors can be replaced with one or more flow sensors positioned within the anchor 501. In some embodiments, the user (e.g., physician) can adjust the amount of occlusion achieved by the anchor 501 based on the readings from the sensor(s).

Figure 19:
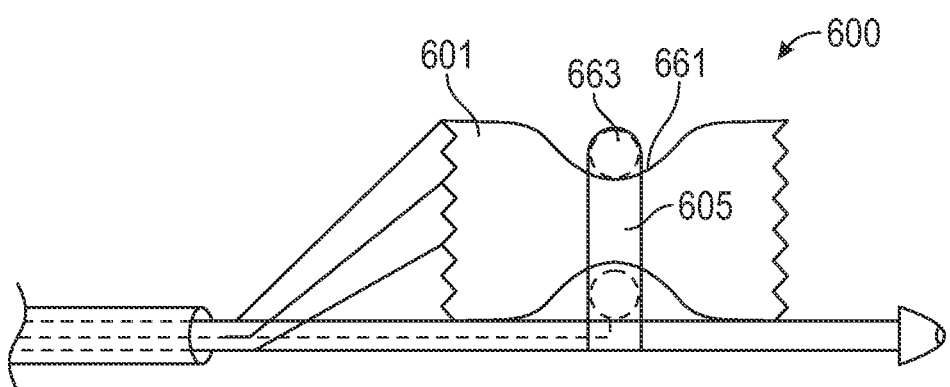
FIG. 19 is a side view of still another embodiment of a blood flow control device.

Another exemplary blood flow control device 600 is shown in FIG. 19. The blood flow control device 600 is similar to device 300 except that the anchor 601 includes a central flexible section 661 that is configured to compress radially upon constriction. For example, in one embodiment (shown in FIG. 19), the device 600 can include an annular balloon 663 positioned around the central flexible section 661. The annular balloon 663 can be inflated and deflated to vary the constriction placed on the flow channel 605.

Figure 20:
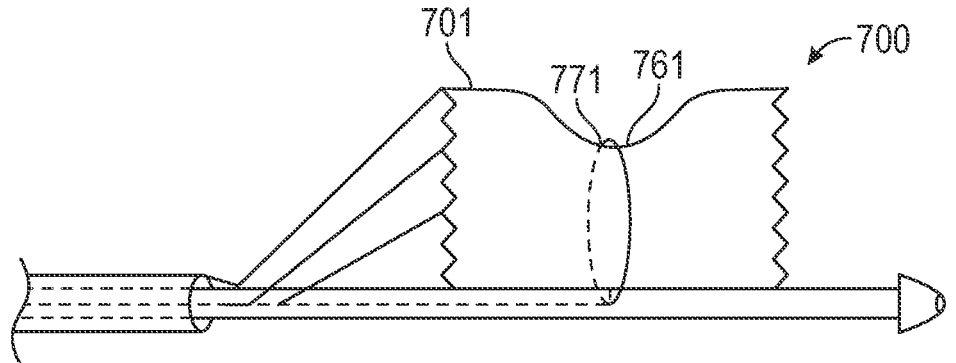
FIG. 20 is a side view of another embodiment of a blood flow control device.

Another exemplary blood flow control device 700 is shown in FIG. 20. The blood flow control device 700 is similar to device 600 except that the balloon 663 is replaced with a lasso 771 (or other mechanically constricting device). The lasso 771 can be configured, when pulled from the proximal end (e.g., via a pullwire, cable, or thread), to decrease the radius of the central flexible section 761 and thereby increase the occlusion achieved by the anchor 701.

Figure 21:
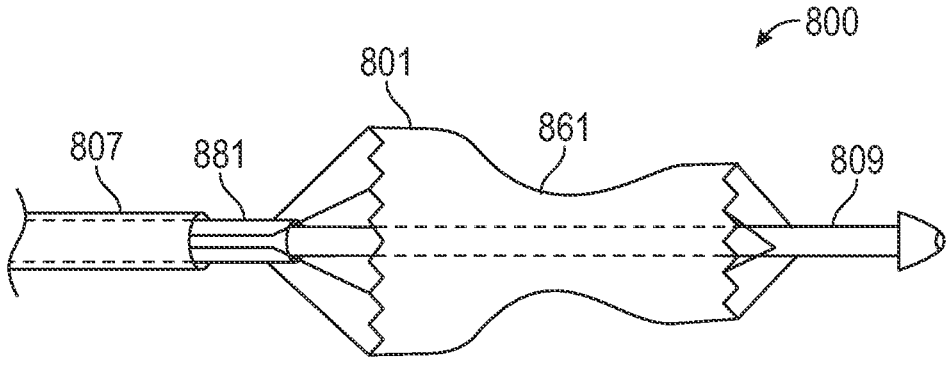
FIG. 21 is a side view of yet another embodiment of a blood flow control device.
Figure 22:
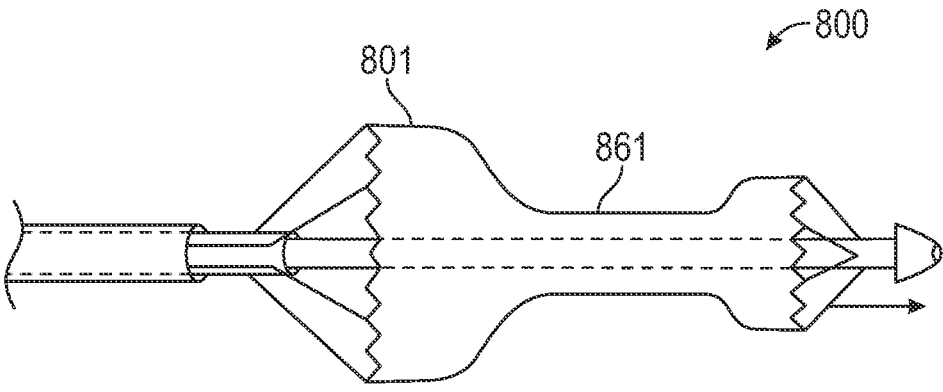
FIG. 22 is a side view of the embodiment of FIG. 21 in a reduced blood flow path configuration.

Another exemplary blood flow control device 800 is shown in FIGS. 21-22. The blood flow control device 800 is similar to device 600 except that the anchor 801 is positioned around the catheter 809 (rather than being attached laterally), and the flexible section 861 is configured to constrict by axially tensioning the anchor 801. That is, the anchor 801 is configured to compress as the anchor 801 is placed under axial tension to vary the flow therethrough. The distal end of the anchor 801 can be attached to the catheter 809, and the proximal end of the anchor 801 can be attached to a middle shaft 881 that extends between the sheath 807 and the catheter 809. As the distance between the distal end of the anchor 801 and the proximal end of the anchor 801 is increased (via relative movement of the catheter 809 and the middle shaft 881), the flexible section 861 can neck down, decreasing or eliminating flow through the anchor 801 (see the transition from FIG. 21 to FIG. 22). In an alternative embodiment, the distal end of the anchor 801 can be rotated relative to the proximal end (e.g., via relative rotation of the catheter 809 and the middle shaft 881) in order to twist the flexible section 861, resulting in a narrowing of flexible section 861.

Figure 23:
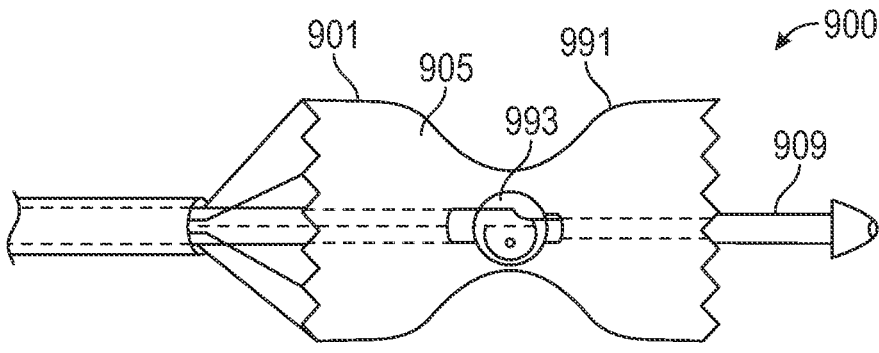
FIG. 23 is a side view of still another embodiment of a blood flow control device.

FIG. 23 shows another exemplary blood flow control device 900. Like device 800, the device 900 includes an anchor 901 that is positioned around a catheter 909. The anchor 901 includes an hourglass shape (i.e., includes a central portion 991 with a reduced cross-section) and an interior inflatable element 993 that is configured to inflate or deflate to increase or decrease the flow rate through the channel 905.

Figure 24:
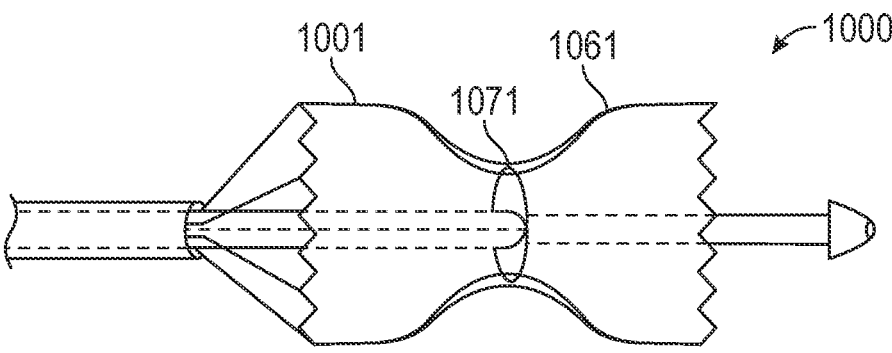
FIG. 24 is a side view of another embodiment of a blood flow control device.

FIG. 24 shows another exemplary blood flow control device 1000. The blood flow control device 1000 is similar to device 900 except that the inflatable element 993 is replaced with a lasso 1071 positioned within or around a flexible section 1061 of the anchor 1001, similar to as described with respect to device 700.

Figure 25:
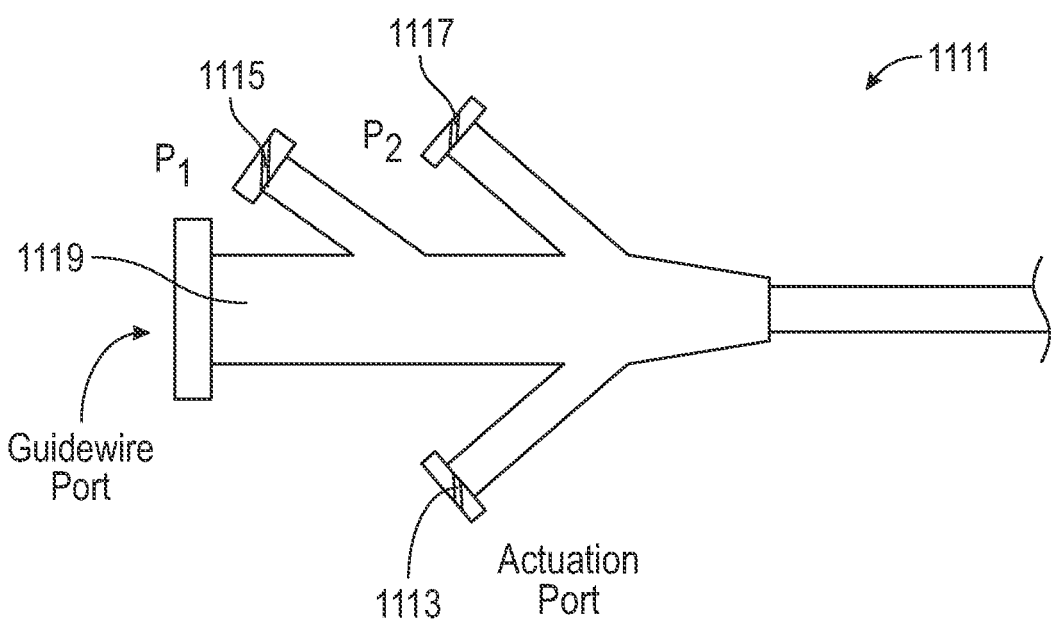
FIG. 25 is a side view of a handle for use with a blood flow control device.

FIG. 25 shows an exemplary handle 1111 for any of the blood flow control devices described herein. The handle 1111 includes an actuation port 1113 that provides a location for pneumatic or mechanical actuation (as described herein). Additionally, the handle 1111 includes ports 1115 and 1117 that provide access for pressure measuring transducers (e.g., to measure the pressure at P1 and P2). Finally, the handle 1111 includes a guidewire port 1119 that can have a rotating hemostatic valve therearound.

Figure 26:
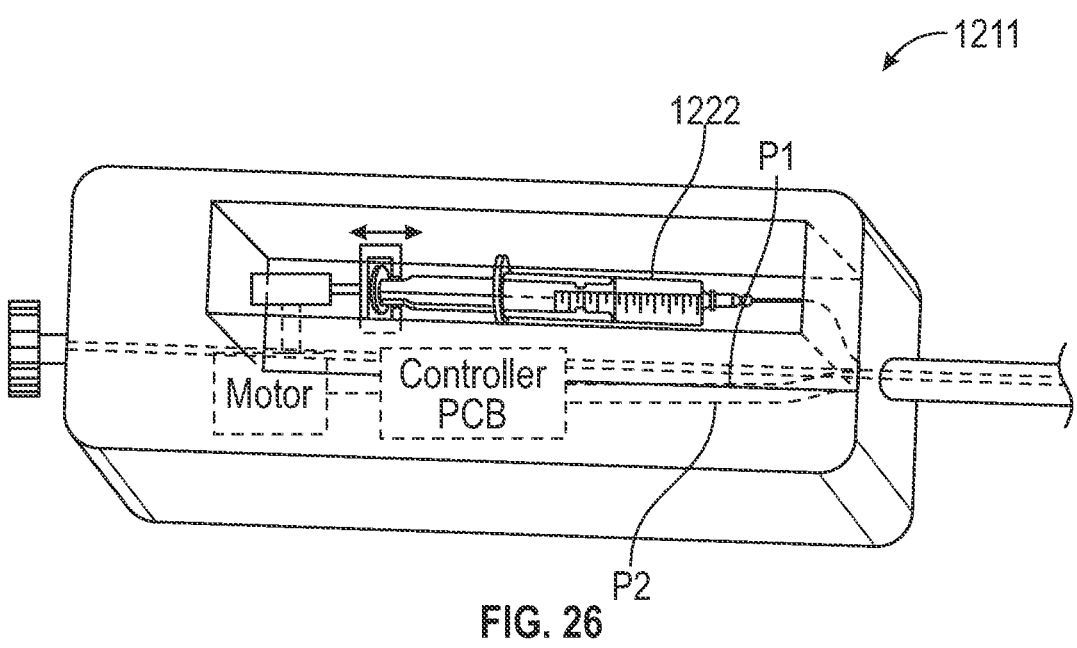
FIG. 26 is a perspective view of another handle for use with a blood flow control device.

FIG. 26 shows another exemplary handle 1211 for any of the blood flow control devices described herein. The handle 1211 can be configured to automatically adjust the amount of occlusion achieved by the occlusion device. For example, the variable occlusion can be controlled by a syringe 1222 within the handle 1211 (e.g., for controlling pneumatic actuation of the occlusion device). The syringe plunger position can be adjusted mechanically by a motor, and the motor can be controlled by a controller that has sensor input from two pressure sensors sensing blood pressure proximal and distal to the anchor.

In some embodiments, the syringe can be replaced with a mechanical actuator (e.g., for controlling mechanic actuation of the occlusion device). For example, the cinch line(s) of the flow control element may be attached to a rotatable knob in the handle. Turning the knob would actuate by spooling or unspooling the cinch line(s) of the flow control element to change the shape of the anchor and the blood flow path. Alternatively, the cinch line(s) could be attached to a lever such that movement of the lever forward or backward would alter the tension on the cinch line(s) to change the shape of the anchor and the blood flow path.

Figure 27:
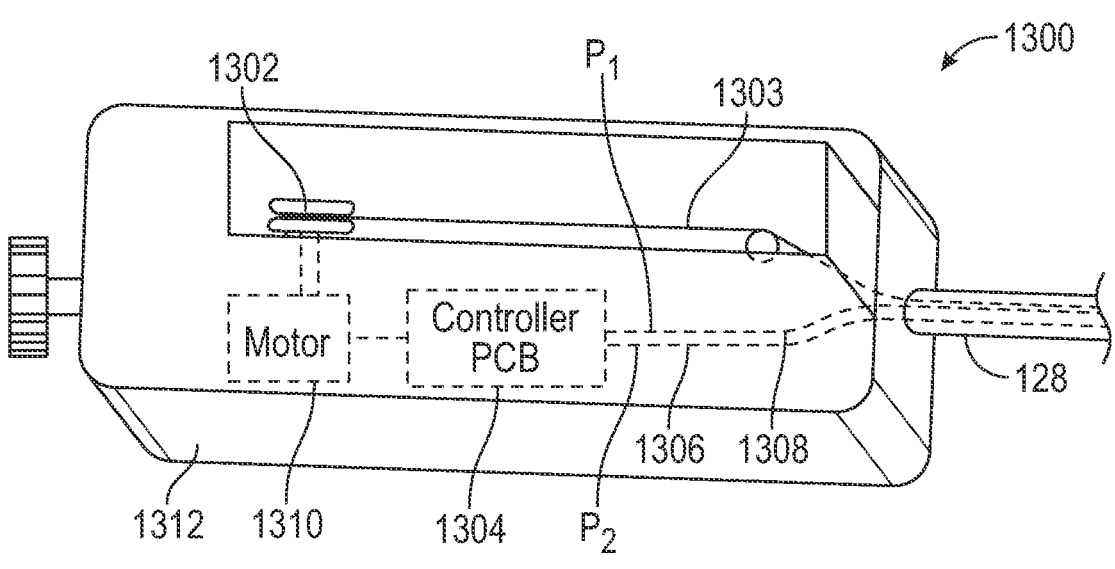
FIG. 27 is a perspective view of yet another handle for use with a blood flow control device.

FIG. 27 shows an embodiment of a cinch line actuator for use with embodiments of the blood flow control device describe above. Actuator 1300 has a spool 1302 around which the cinch line(s) 1303 are wrapped. A controller 1304 uses pressure information from two pressure sensors (not shown) communicated by lines 1306 and 1308 to operate a motor 1310 to turn spool 1302. The actuator 1300 may be disposed within a handle 1312 to which the blood flow control device's catheter 128 is connected.

Figure 28:
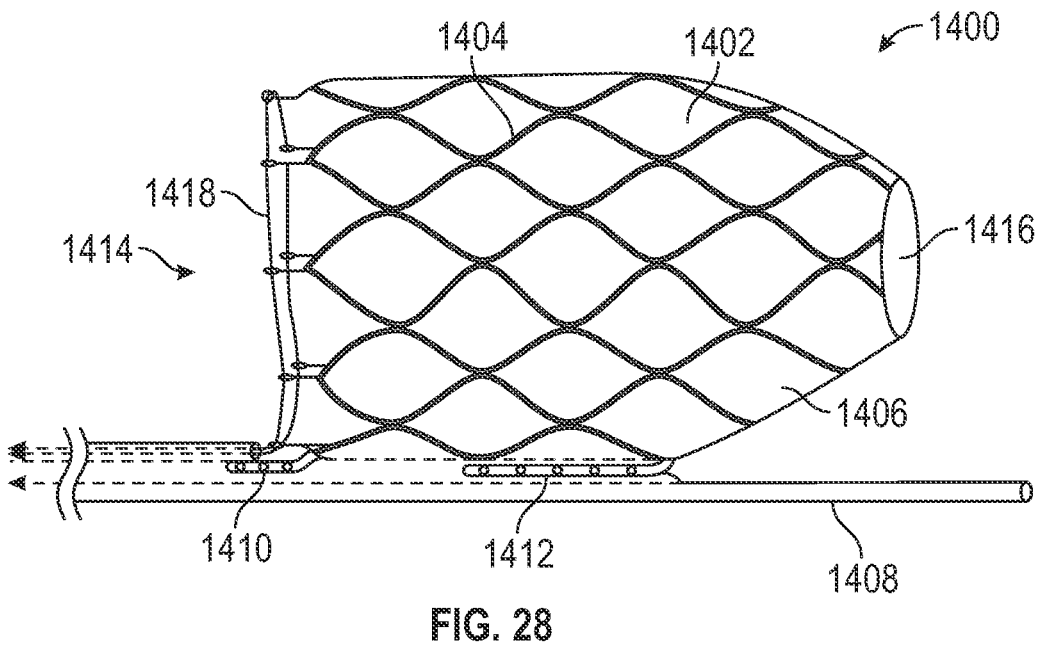
FIG. 28 is a perspective view of another embodiment of a blood flow control device.

FIG. 28 shows an embodiment of a blood flow control device 1400 providing a constant amount of occlusion of the blood vessel in which it is deployed. Anchor 1402 is heat set to be in a shape that is larger at its proximal end than at its distal end, such as the shape shown in in FIG. 28. As in those earlier embodiments, anchor 1402 has a stent 1404 that may serve as the scaffold of anchor 1402, and stent 1404 may be covered on the outside and/or on the inside by a blood impermeable material 1406. Stent 1404 may be formed from a shape memory material such as Nitinol. Stent 1404 may be attached to a catheter 1408 via proximal and distal catheter attachment elements 1410 and 1412, as described above with respect to earlier embodiments. This embodiment may also employ lumens within catheter 1408 to communicate between pressure ports (not shown) on the catheter proximal and distal to anchor 1402 and pressure sensors (not shown) at the proximal end of catheter 1408. When in place in the blood vessel, anchor 1402 expands to engage the inside wall of the blood vessel (e.g., the IVC or the SVC), and blood flows along a blood flow path into a proximal opening 1414, through the interior of the anchor and out of a distal opening

1416 smaller than the proximal opening. For example, proximal opening 1414 may be 20-30 mm in diameter (i.e., large enough to expand to engage the wall of the IVC or the SVC), and distal opening 1416 may have a diameter of 4-10 mm. The clinician may choose a device that will provide the desired amount of occlusion, and therefore the desire pressure gradient, based on the sizes of the proximal and distal openings The embodiment of FIG. 28 employs an anchor collapse control element to facilitate collapse of the anchor 1402 and placement of the collapsed anchor within the a delivery sheath. As in the earlier embodiments, a collapsing line 1418 threaded through the proximal end of stent 1404 (e.g., through loops formed in, or attached to, the proximal ends of the proximal cells of the stent) serves as an anchor collapse control element. The two sides of collapsing line 1418 extend through a lumen of catheter 1408 where its two ends can be drawn proximally to collapse the proximal end of anchor 1402 and draw it into the delivery sheath. Collapsing line 1418 may be, e.g., a polymer fiber (monofilament or braided polymer line) or a flexible metal wire or cable.

The blood flow control devices described herein can be used in the SVC or IVC temporarily (e.g., for 8-72 hours) to decrease cardiac filling pressures and preload on the right heart. For example, the flow occlusion devices described herein can be placed in an infrarenal location of the IVC, which may advantageously additionally decrease the renal vein pressure, thereby increasing diuretic effectiveness. The flow occlusion devices described herein can be used to maintain a desired pressure differential thereacross. Advantageously, the flow occlusion devices described herein can achieve variable occlusion, enabling the user (e.g., physician) to adjust the occlusion as desired.

Any or all of the blood flow control devices described above may have anchors that self-expand to 28 mm diameter with sufficient outward expansion force, and the device may be compressed to a size less than 16 Fr. The adjustable blood flow control devices described above may be controlled to restrict the blood flow area from a fully open configuration of 14 mm diameter to a fully closed configuration. The devices may have a length of 4 cm. The catheter may have a built-in loading sheath for introduction into a 16 Fr venous sheath.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A blood flow control device comprising:
a catheter adapted to be advanced into a blood vessel to a blood flow control site within the blood vessel, the catheter including a lumen disposed therein in communication with a port in a sidewall of the catheter;
an expandable anchor supported by the catheter, the expandable anchor being adapted to expand to engage a wall of the blood vessel, the expandable anchor comprising a blood impermeable wall defining an adjustable blood flow path extending through the expandable anchor from a proximal opening to a distal opening, the catheter being entirely disposed outside of the adjustable blood flow path, the expandable anchor further comprising at least one catheter attachment element slidably disposed within the lumen via the port and configured to permit at least one end of the expandable anchor to move longitudinally with respect to the catheter when the expandable anchor expands or collapses; and
a flow control element supported by the catheter, the flow control element being adapted to change a dimension of the adjustable blood flow path to change a rate of blood flow through the adjustable blood flow path.

2. The blood flow control device of claim 1, wherein the adjustable blood flow path of the expandable anchor is disposed at the distal opening such that the distal opening has a smaller open area than an open area of the proximal opening.

3. The blood flow control device of claim 1, wherein the adjustable blood flow path of the expandable anchor is disposed between the proximal opening and the distal opening.

4. The blood flow control device of claim 1, wherein the expandable anchor is disposed on an exterior side of the catheter at a distal section of the catheter such that the catheter is outside of the anchor.

5. The blood flow control device of claim 1, wherein the at least one catheter attachment element is disposed at a proximal end of the expandable anchor.

6. The blood flow control device of claim 1, wherein the at least one catheter attachment element is disposed at a distal end of the expandable anchor.

7. The blood flow control device of claim 1, wherein the expandable anchor comprises a self-expandable scaffold.

8. The blood flow control device of claim 1, wherein the blood impermeable wall comprises a blood impermeable covering disposed on at least one of an interior surface and an exterior surface of the expandable anchor and surrounding the adjustable blood flow path.

9. The blood flow control device of claim 1, further comprising an anchor collapse control element supported by the catheter and adapted to reduce a dimension of the expandable anchor to facilitate placement of the expandable anchor in a sheath.

10. The blood flow control device of claim 9, wherein the anchor collapse control element is supported by the catheter outside of the adjustable blood flow path.

11. The blood flow control device of claim 9, further comprising an anchor collapse actuator disposed at a proximal section of the catheter and adapted to actuate the anchor collapse control element.

12. The blood flow control device of claim 9, wherein the anchor collapse control element is adapted to reduce a cross-sectional dimension of a proximal end of the expandable anchor.

13. The blood flow control device of claim 12, wherein the anchor collapse control element comprises a line slidingly disposed in a plurality of loops on the proximal end of the expandable anchor and extending proximally through a lumen of the catheter.

14. The blood flow control device of claim 13, wherein the loops are integral with the expandable anchor.

15. The blood flow control device of claim 1, further comprising a blood flow control actuator disposed at a proximal section of the catheter and adapted to actuate the flow control element.

16. The blood flow control device of claim 1, wherein the flow control element is supported by the catheter outside of the adjustable blood flow path.

17. The blood flow control device of claim 1, wherein the flow control element comprises a cinching line extending proximally from the expandable anchor and adapted to reduce a diameter of at least a portion of the expandable anchor.

18. The blood flow control device of claim 1, wherein the expandable anchor is fixedly attached to the catheter.

* * * * *